US011191902B2

(12) United States Patent
Dungar et al.

(10) Patent No.: US 11,191,902 B2
(45) Date of Patent: Dec. 7, 2021

(54) COMBINATION PLUNGER DEVICE FOR A DUAL CHAMBER MIXING SYRINGE

(71) Applicant: UNL Holdings LLC, New York, NY (US)

(72) Inventors: Peter J. Dungar, York, PA (US); Molly M. Weaver, Glenmoore, PA (US); Philip A. Weaver, Denver, PA (US); Katlin M. Lumme, Marietta, GA (US); Robert E. Johannesson, Lansdale, PA (US)

(73) Assignee: UNL HOLDINGS LLC, New York, NY (US)

( * ) Notice: Subject to any disclaimer, the term of this patent is extended or adjusted under 35 U.S.C. 154(b) by 0 days.

(21) Appl. No.: 16/161,759

(22) Filed: Oct. 16, 2018

(65) Prior Publication Data

US 2019/0217010 A1 Jul. 18, 2019

Related U.S. Application Data

(62) Division of application No. 14/648,376, filed as application No. PCT/US2013/070494 on Nov. 18, 2013, now Pat. No. 10,130,768.

(Continued)

(51) Int. Cl.
*A61M 5/28* (2006.01)
*A61M 5/19* (2006.01)
(Continued)

(52) U.S. Cl.
CPC ............ *A61M 5/284* (2013.01); *A61J 1/2093* (2013.01); *A61M 5/19* (2013.01); *A61M 5/3148* (2013.01);
(Continued)

(58) Field of Classification Search
CPC ...... A61M 5/284; A61M 5/19; A61M 5/3148; A61M 5/3234; A61M 2005/3117;
(Continued)

(56) References Cited

U.S. PATENT DOCUMENTS 2,591,706 A 4/1952 Lockhart
3,066,670 A 12/1962 Stauffer
(Continued)

FOREIGN PATENT DOCUMENTS

CN 2577863 Y 5/2007
CN 102143776 A 8/2011
(Continued)

OTHER PUBLICATIONS

European Patent Office, Extended European Search Report for European Patent Application No. 13799451.3, entitled: "Combination Plunger Device for a Dual Chamber Mixing Syringe," dated Mar. 25, 2015, 5 pages, Munich, Germany.
(Continued)

*Primary Examiner* — Amber R Stiles
(74) *Attorney, Agent, or Firm* — Hamilton, Brook, Smith & Reynolds, P.C.

(57) ABSTRACT

A combination plunger, a mixing device and a mixing syringe including the same are provided. The mixing syringe includes concentric outer and inner barrels that form an outer chamber, the inner barrel having an inner chamber. The combination plunger includes a mixing plunger and a delivery plunger and a biasing means. The mixing plunger is slidably located in the outer chamber and translated by coordinated depression of the delivery plunger to transfer a first substance from the outer chamber to mix with a second substance in the inner chamber. After the mixing stage is complete, the delivery plunger is disengaged from the mixing plunger and permitted, such as by rotation, to be further (Continued)

depressed in the axial direction to deliver fluid contents of the mixing syringe to a recipient. The mixing syringe needle is then retracted as result of engagement by the delivery plunger and activation of the biasing means.

11 Claims, 24 Drawing Sheets

Related U.S. Application Data

(60) Provisional application No. 61/731,972, filed on Nov. 30, 2012.

(51) Int. Cl.
| | |
|---|---|
| A61M 5/31 | (2006.01) |
| A61J 1/20 | (2006.01) |
| A61M 5/32 | (2006.01) |
| B01F 11/00 | (2006.01) |
| B01F 13/00 | (2006.01) |
| B01F 15/02 | (2006.01) |
| B01F 15/00 | (2006.01) |
| A61M 5/315 | (2006.01) |

(52) U.S. Cl.
CPC ....... *A61M 5/3234* (2013.01); *B01F 11/0054* (2013.01); *B01F 11/0082* (2013.01); *B01F 13/0023* (2013.01); *B01F 15/00279* (2013.01); *B01F 15/0224* (2013.01); *A61M 5/3221* (2013.01); *A61M 2005/3117* (2013.01); *A61M 2005/31598* (2013.01); *A61M 2005/3231* (2013.01); *A61M 2005/3238* (2013.01); *A61M 2202/0007* (2013.01); *A61M 2207/00* (2013.01)

(58) Field of Classification Search
CPC ........ A61M 5/3221; A61M 2202/0007; A61M 2005/3231; A61M 2005/3238; A61M 2207/00; A61M 2005/31598; A61J 1/2093; B01F 11/0054; B01F 11/0082; B01F 13/0023; B01F 15/0224; B01F 15/00279

See application file for complete search history.

(56) References Cited

U.S. PATENT DOCUMENTS

| | | |
|---|---|---|
| 3,662,753 A | 5/1972 | Tassell |
| 3,739,947 A | 6/1973 | Baumann et al. |
| 3,749,084 A | 7/1973 | Cucchiara |
| 3,872,864 A | 3/1975 | Allen, Jr. |
| 4,188,949 A | 2/1980 | Antoshkiw |
| 4,411,163 A | 10/1983 | White |
| 4,643,723 A | 2/1987 | Smit |
| 4,655,747 A | 4/1987 | Allen, Jr. |
| 4,820,275 A | 4/1989 | Haber et al. |
| 4,834,714 A | 5/1989 | Lascar et al. |
| 5,078,691 A | 1/1992 | Hamacher |
| 5,211,285 A | 5/1993 | Haber et al. |
| 5,300,030 A | 4/1994 | Crossman et al. |
| 5,312,336 A | 5/1994 | Haber et al. |
| 5,395,326 A | 3/1995 | Haber et al. |
| 5,496,284 A | 3/1996 | Waldenburg |
| 5,593,391 A | 1/1997 | Stanners |
| 5,643,206 A | 7/1997 | Fischer |
| 5,785,682 A | 7/1998 | Grabenkort |
| 5,807,323 A | 9/1998 | Kriesel et al. |
| 5,851,197 A | 12/1998 | Marano et al. |
| 5,971,953 A | 10/1999 | Bachynsky |
| 6,027,482 A | 2/2000 | Imbert |
| 6,132,400 A | 10/2000 | Waldenburg |
| 6,248,095 B1 | 6/2001 | Giambattista et al. |
| 6,387,078 B1 | 5/2002 | Gillespie, III |
| 6,491,667 B1 | 12/2002 | Keane et al. |
| 6,793,646 B1 | 9/2004 | Giambattista et al. |
| 7,112,188 B2 | 9/2006 | Waldenburg |
| 7,169,132 B2 | 1/2007 | Bendek et al. |
| 7,399,295 B2 | 7/2008 | Waldenburg |
| 7,402,150 B2 | 7/2008 | Matsumoto et al. |
| 7,935,087 B2 | 5/2011 | Judd et al. |
| 8,021,333 B2 | 9/2011 | Kaal et al. |
| 8,096,971 B2 | 1/2012 | Bassarab et al. |
| 8,945,048 B2 | 2/2015 | Thorley et al. |
| 9,254,365 B2 | 2/2016 | Thorley et al. |
| 9,539,393 B2 | 1/2017 | Johannesson |
| 10,130,768 B2 | 11/2018 | Dungar et al. |
| 2002/0035348 A1 | 3/2002 | Hjertman |
| 2002/0177805 A1 | 11/2002 | Barker et al. |
| 2002/0183690 A1 | 12/2002 | Arnisolle |
| 2004/0097874 A1 | 5/2004 | Griffiths et al. |
| 2004/0236273 A1 | 11/2004 | Tanaka et al. |
| 2005/0054980 A1 | 3/2005 | Targell |
| 2005/0154357 A1 | 7/2005 | Pinel |
| 2005/0277886 A1 | 12/2005 | Hommann et al. |
| 2006/0052747 A1* | 3/2006 | Nishimura ........ A61M 5/31596 604/85 |
| 2006/0062736 A1* | 3/2006 | Wright ............. A61B 17/00008 424/45 |
| 2006/0111666 A1 | 5/2006 | Hommann et al. |
| 2007/0270710 A1 | 11/2007 | Frass et al. |
| 2010/0047914 A1 | 2/2010 | Peyman et al. |
| 2010/0082015 A1 | 4/2010 | Chebator |
| 2010/0094214 A1 | 4/2010 | Abry et al. |
| 2010/0106138 A1 | 4/2010 | Chavarria |
| 2010/0249753 A1 | 9/2010 | Gaisser et al. |
| 2010/0298811 A1 | 11/2010 | Connair |
| 2011/0251553 A1 | 10/2011 | Ratjen et al. |
| 2012/0029471 A1 | 2/2012 | Lee et al. |
| 2012/0053516 A1 | 3/2012 | Cronenberg et al. |
| 2012/0205507 A1 | 8/2012 | Sato et al. |
| 2012/0296276 A1 | 11/2012 | Nicholls et al. |
| 2013/0060231 A1 | 3/2013 | Adlon et al. |
| 2013/0060232 A1 | 3/2013 | Adlon et al. |
| 2015/0320935 A1 | 11/2015 | Dungar et al. |
| 2017/0080155 A1 | 3/2017 | Johannesson |

FOREIGN PATENT DOCUMENTS

| | | |
|---|---|---|
| CN | 102648014 A | 8/2012 |
| CN | 102695533 A | 9/2012 |
| FR | 2741810 A1 | 11/1995 |
| JP | H02-302265 A | 12/1990 |
| JP | H08-150208 | 6/1996 |
| JP | 2005-508202 A | 3/2005 |
| JP | 2011-509810 A | 3/2011 |
| JP | 2012-210458 A | 11/2012 |
| TW | 201125609 A | 8/2011 |
| WO | WO 2000/024441 A1 | 5/2000 |
| WO | WO 2000/062839 A2 | 10/2000 |
| WO | WO 2002/072171 A2 | 9/2002 |
| WO | WO 2005/013830 A1 | 2/2005 |
| WO | WO 2005/072801 A1 | 8/2005 |
| WO | WO 2006/058435 A1 | 6/2006 |
| WO | WO 2006/108243 A2 | 10/2006 |
| WO | WO 2006/119570 A1 | 11/2006 |
| WO | WO 2008/087071 A1 | 7/2008 |
| WO | WO 2009/003234 A1 | 1/2009 |
| WO | WO 2010/135732 A1 | 11/2010 |
| WO | WO 2011/060541 A1 | 5/2011 |
| WO | WO 2011/075760 A1 | 6/2011 |

OTHER PUBLICATIONS

European Patent Office, as International Searching Authority, International Search Report and Written Opinion, from International PCT Application No. PCT/US2013/070494, entitled: "Combination Plunger For Dual Chamber Mixing Syringe," dated (Apr. 3, 2014), pp. 1-17.

(56) References Cited

OTHER PUBLICATIONS

International Searching Authority, International Search Report and Written Opinion for PCT/AU2012/000925, entitled: "Dual-chamber Mixing Device for a Syringe," dated Oct. 5, 2012, 13 pages, Australia.
International Searching Authority, Written Opinion for PCT/AU2012/001029, entitled: "Automatic Reconstitution for Dual Chamber Syringe," dated Oct. 19, 2012, 5 pages, Australia.
International Searching Authority, International Search Report for PCT/AU2012/001029, entitled: "Automatic Reconstitution for Dual Chamber Syringe," dated Aug. 31, 2012, 6 pages, Australia.
Non-Final Office Action for U.S. Appl. No. 14/648,376, dated Sep. 15, 2017.
Notice of Allowance for U.S. Appl. No. 14/648,376, dated Mar. 20, 2018.
Notice of Allowance for U.S. Appl. No. 14/648,376, dated Jul. 16, 2018.
Taiwan Patent Office, Examination Report in TW Application No. 101131792, entitled: "Automatic recovery structure of dual chamber injector and its combination method," dated (Jun. 3, 2015) 27 pgs.

* cited by examiner

COMBINATION PLUNGER DEVICE FOR A DUAL CHAMBER MIXING SYRINGE

RELATED APPLICATION(S)

This application is a divisional of U.S. application Ser. No. 14/648,376, which is the U.S. National Stage Application of International Application No. PCT/US2013/070494 filed on Nov. 18, 2013, published in English, which claims the benefit of U.S. Provisional Application No. 61/731,972, filed on Nov. 30, 2012. The entire teachings of the above applications are incorporated herein by reference.

BACKGROUND

It is known to provide syringes that comprise a mixing device for mixing deliverable substances prior to injection. This allows, for example, a diluent to be added to a dehydrated, lyophilized, desiccated or powdered active substance immediately prior to injection, which is particularly useful for substances that are subject to degradation or loss of activity when stored in a hydrated form.

The majority of mixing devices for syringes utilize sequential chambers, wherein the syringe has one barrel having a first proximal chamber and a second distal chamber separated by, for example, a membrane or elastomeric seal. A number of such sequential-chamber mixing syringes utilize a bypass protrusion at a section of the barrel to enable fluid in the proximal chamber to bypass the dividing membrane and mix with the fluid or powder in the distal chamber.

However, some mixing syringes utilize concentric barrel configurations. The concentric barrel mixing syringes to date, however, require complex assemblies, multiple operation steps by the user, or other particular nuances that make them difficult to manufacture, assemble, or operate. For examples, some existing concentric barrel mixing syringes require concentric inner and outer barrels that are selectively rotatable with respect to each other, and require one or more sealing rings which contain a passage means therein. The barrels must be rotated to align a hole in the inner barrel with the passage means in a sealing ring. The passage means in the sealing ring includes a radially extending opening through the sealing ring and a groove extending longitudinally of the sealing ring from the radially extending opening. This arrangement being such that the groove connects the outer barrel with the radially extending opening and the radially extending opening selectively connects the groove with the hole in the inner barrel. This enables flow of fluid from the outer barrel into the inner barrel to thereby mix the fluid with a substance in the inner barrel. Such configurations require complex components and cumbersome requirements for the user to operate the device.

Other concentric barrel designs utilize outer and inner telescopic tubular elements seated inside a barrel and coaxial with the longitudinal axis. The outer tubular element and barrel form a chamber which holds a reservoir of liquid. The outer tubular element has a fluid passageway therein that allows the liquid to flow from the chamber into the inner tubular element. The inner tubular element has an end nearby the injection port with a seal thereon that has an orifice therein. This inner tubular element receives the end of the plunger with the resilient seal thereon. Accordingly, such mixing syringe configurations require three tubular elements, with the outer and inner concentric chambers residing inside a third barrel.

There are numerous complexities associated with the use of concentric barrels for mixing syringe configurations. In addition to those described above, mixing syringes utilizing concentric barrels must also address factors such as maintenance of container sterility, interaction of components for sealing, venting requirements, and distribution of internal forces, among others. Some dual chambered syringes have concentric inner and outer barrels that form an annular space to hold a fluid and utilize one or more apertures between the inner and outer barrels to enable flow of a liquid from the annular space into the inner barrel and thereby mix the liquid with a substance in the inner barrel. The liquid is forced from the annular into the inner barrel by depression of a plunger slidably movable in the annular space. First and second sealing bands are slidably received about the inner barrel in the annular space and are mutually spaced therealong. The position of the sealing bands can dictate how sterility of the fluid path is maintained, how internal forces are distributed, and how venting occurs. For example, both of the sealing bands may be initially positioned above the aperture to form a sealed annular volume for the first liquid component. Because of this arrangement, the aperture also must act as a vent to enable any air in the annular space distal to the second sealing band, which space must be sterilized, to be expelled via the aperture upon depression of the plunger. This venting requirement may cause difficulties and require additional equipment and processing steps, such as requiring filling the inner chamber under vacuum to remove all air from the inner chamber and the distal portion of the outer barrel below the second reconstitution seal.

Generally, prior art mixing devices comprising concentric barrels are complicated in structure and often require rotation of the barrels to align one or more apertures that enable a flow of a liquid substance from one chamber into another. Further to this, various sterility, sealing and venting arrangements have been used which have serious limitations in terms of ease of manufacture and operation of the mixing device.

SUMMARY

It is therefore an object of the invention to provide a combination plunger device and/or a mixing syringe having a combination plunger device that alleviates one or more of the problems associated with prior art mixing devices and/or syringes, such as those referred to above.

The invention is broadly directed to a combination plunger for a mixing syringe, wherein the combination plunger comprises a mixing plunger and a delivery plunger that are capable of coordinated and/or synchronous movement during at least a portion of the operation of the combination plunger.

A first aspect of the invention provides a combination plunger for a syringe mixing device, said combination plunger comprising: a mixing plunger and a delivery plunger are releasably engaged to facilitate coordinated or synchronous axial movement of the mixing plunger and the delivery plunger for at least a portion of operation of the combination plunger; and a pill housing having a biasing member.

Suitably, axial movement, travel or translation of the delivery plunger conveys or causes axial movement or travel of the mixing plunger until disengagement of the mixing plunger and the delivery plunger. In at least one embodiment, elements of the mixing plunger and the delivery plunger are removably engageable to permit coordinated or synchronous travel of the mixing plunger and delivery plunger as a combination plunger for at least a portion of operation, and are capable of subsequently being disengaged to permit separate or independent axial movement or travel of one or both components. In at least one embodiment, the delivery plunger may be rotatably disengaged from the mixing plunger. Preferably, disengagement of the mixing plunger and delivery plunger permits or facilitates separate or independent axial travel, movement or translation of the delivery plunger. In particular embodiments, the mixing plunger may have one or more connection members substantially at a proximal end thereof. The delivery plunger may have one or more connection recesses which correspond with, engage or receive respective connection members of the mixing plunger. When releasably engaged, the connection between the connection members of the mixing plunger and the connection recesses of the delivery plunger permit the delivery plunger and mixing plunger to axially move or travel as combination plunger (i.e., as a unified plunger). Release of the connection members of the mixing plunger and the connection recesses of the delivery plunger facilitate independent axial movement of the delivery plunger. In at least one embodiment, this may include axial rotation of the delivery plunger relative to the mixing plunger.

In at least one embodiment the combination plunger comprises one or more locks or locking systems. As previously described, the respective connection members of the mixing plunger and the connection recesses of the delivery plunger form a lock which releasably couples the delivery plunger and mixing plunger. One further embodiment of a lock comprises locking members that initially, releasably couple the pill housing and the mixing plunger to retain the biasing member in an initially energized state. Another further embodiment of a lock comprises a locking member (e.g., a cam clip) that prevents rotation of the delivery plunger until disengagement from the mixing plunger. Yet another further embodiment of a lock comprises a locking member (e.g., locking fingers or prongs), which upon completion of mixing by the mixing plunger, locks the mixing plunger in place while permitting axial travel, movement or translation of the delivery plunger. In other embodiments, the combination plunger may optionally comprise one or more of: a button at a proximal end of the delivery plunger, biasing surfaces, chamfers, prongs, lips, abutments and the like which may correspond with, receive or engage the locks disclosed herein, and/or any combination thereof.

Suitably, the combination plunger is operably connectable to a mixing device of a mixing syringe, as will be described in more detail hereinafter). In one embodiment, the combination plunger may further comprise a flange connector for connecting the combination plunger to the mixing device. The flange connector may further comprise finger flanges which extend substantially radially from the flange connector.

In one embodiment, the combination plunger and a barrel extension of a mixing device or mixing syringe (described in more detail hereinafter) are engageable to form a mixing syringe having the combination plunger mounted thereto.

When the combination plunger is mounted to the mixing syringe, the biasing member of the combination plunger is operable to facilitate retraction of a needle or needle assembly of the mixing syringe. The biasing member may be a spring, elastic or other member capable of storing and releasing energy to facilitate motion of one or more components of the combination plunger. In at least one embodiment, the biasing member is a compression spring. In an embodiment, the combination plunger may comprise one or more flex members that engage one or more recesses of the pill housing to initially maintain the biasing member in an energized state within the pill housing. Upon disengagement of the one or more flex members (such as by the delivery plunger or a button thereof) from the one or more recesses of the pill housing, the biasing member is permitted to expand in a proximal direction (i.e., towards a user). The expansion of the biasing member, substantially simultaneous with, or subsequent to, engagement between the delivery plunger or a delivery plunger seal and one or more components of a needle assembly, such as a needle, enables retraction of the needle or needle assembly into the barrel of the syringe.

In another aspect, the invention provides a mixing device comprising the combination plunger of the first-mentioned aspect.

One embodiment provides a mixing device for a mixing syringe, wherein the mixing device comprises: an outer barrel and an inner barrel in a substantially coaxial relationship that form an outer chamber; and the combination plunger of the first aspect, wherein the mixing plunger is axially moveable within the outer chamber.

Preferably, the mixing device includes a plurality of seals. Preferably, the plurality of seals comprises a proximal seal and a distal seal. In a preferred embodiment, the plurality of seals comprises: a proximal seal engageably or connectably coupled, connectable or affixed to the mixing plunger and slidably moveable in the outer chamber; and said distal seal initially in a first position in sealing engagement with said one or more fluid paths in the inner barrel and slidably moveable in the outer chamber from sealing engagement with the one or more fluid paths to a second position intermediate or at least partly between said one or more fluid paths and said vent. The movement of the mixing plunger causes movement of the proximal seal to which the plunger is engaged or connectably coupled or affixed. This movement is relayed to the first mixing substance in the outer chamber and, similarly, to the distal seal. Accordingly, axial movement of the mixing plunger indirectly (i.e., without needing direct contact) facilitates axial movement of the distal seal to said second position.

Preferably, the one or more vents are operable to facilitate exit of air from the outer chamber to atmosphere when the mixing plunger and distal seal are slidably moved in the outer chamber. The one or more vents may be integrally formed in said outer barrel or may be a vent cap mounted or affixed to the inner and/or outer barrel. In either embodiment, conduits, holes, porous membranes, collapsible components and the like may be utilized. For example, in at least one embodiment the vent cap is a plastic vent cap comprising one or more vent conduits, which plastic vent cap closes the outer chamber at the distal end of the outer barrel while permitting air to pass through the one or more vent conduits to atmosphere upon depression of the mixing plunger and movement of the distal seal.

In one embodiment, the mixing syringe further comprises a removable safety cap. Preferably, the removable safety cap prevents undesired movement of the distal seal prior to use (e.g., during transportation). The removable safety cap may comprise a plurality of protrusions which are insertable through respective vent conduits so as to be adjacent to, or in contact with, the distal seal. The mixing syringe may further comprise a barrel extension mounted to the outer barrel, or integrally formed with the outer barrel. The barrel extension may, optionally, include flange hooks which facilitate a connection with the flange of the combination plunger device.

Suitably, the mixing device is capable of comprising a plurality of mixing substances wherein at least a first mixing substance is locatable in the outer chamber between the outer barrel and the inner barrel and at least a second mixing substance is locatable in an inner chamber in said inner barrel, the inner barrel comprising one or more fluid paths through which the first mixing substance can enter the inner chamber in the inner barrel to thereby form a mixture with the second mixing substance; one or more vents in fluid communication with said outer chamber; and at least one seal located in said outer chamber which is capable of axial movement from a first position in sealing engagement with said one or more fluid paths in the inner barrel to a second position at least partly between said one or more fluid paths and said one or more vents. In at least one embodiment, the inner barrel and the outer barrel are non-rotatable with respect to each other. The mixing plunger may be axially moveable within the outer chamber between the outer barrel and the inner barrel to facilitate entry of the at least first mixing substance into the inner chamber in the inner barrel and to facilitate axial movement of said seal from a first position in sealing engagement with said one or more fluid paths in the inner barrel to said second position intermediate or at least partly between said one or more fluid paths and said vent. The syringe may be utilized for storing, transporting, mixing, and injecting one or more mixing substances to treat a patient. As will be described further below, the syringe may further contain safety features which retract the needle after use, providing desirable needle-stick prevention, and prevent re-use of the syringe.

The one or more fluid paths may comprise one or more apertures, holes, bores, ports, pass-throughs or conduits. These may be of any suitable shape, configuration, arrangement and/or number. Preferably, the fluid path comprises a plurality of apertures. The apertures may be radial bores (i.e., normal to the axis of the barrel), angular bores (i.e., at an angle to axis of the barrel), helical (e.g., an angular and radial path as it traverses the thickness of the barrel wall), or any number of other configurations. The number and placement of the apertures, in locational spacing and arrangement, may also be adjusted for the desired mixing characteristics. As such, these parameters of the apertures may be configured to promote the desired mixing, dilution, and other fluid flow characteristics of the mixing syringe. Suitably, in at least one embodiment the mixing device may comprise one or more components substantially as described in International Publication WO2013/020170, although without limitation thereto.

The first and second mixing substances may comprise one or more fluids or one or more solids. The first mixing substance locatable in the outer chamber may be a fluid. The fluid may be a pharmaceutically active fluid or a pharmaceutically inactive fluid, such as a diluent. The second mixing substance locatable in the inner chamber may be a pharmaceutically active solid or a pharmaceutically active or inactive fluid. In one embodiment, the inner chamber contains a pharmaceutically active solid and the outer chamber contains a pharmaceutically inactive diluent, such as water, whereby entry of the diluent through the one or more apertures from outer chamber into the inner chamber facilitates mixing with the pharmaceutically active solid. The interaction between the diluent and the pharmaceutically active solid enables reconstitution of the pharmaceutically active solid for subsequent delivery to a patient. In another embodiment, the inner chamber contains a pharmaceutically active solid and the outer chamber contains a pharmaceutically active fluid, whereby entry of the fluid through the one or more apertures from the outer chamber into the inner chamber facilitates mixing with the pharmaceutically active solid in the inner chamber. The interaction between the pharmaceutically active fluid and the pharmaceutically active solid enables reconstitution of the pharmaceutically active solid for subsequent delivery to a patient. In yet another embodiment, the inner chamber contains a first pharmaceutically active fluid and the outer chamber contains a second pharmaceutically active fluid, whereby entry of the first pharmaceutically active fluid through the one or more from the outer chamber into the inner chamber facilitates mixing with the second pharmaceutically active fluid in the inner chamber. The interaction between the first pharmaceutically active fluid and the second pharmaceutically active fluid enables mixing of the pharmaceutically active fluids for subsequent delivery to a patient. Accordingly, the mixing device may facilitate the storage of multiple component pharmaceutical substances in the outer and inner chambers, thereby maintaining the stability and efficacy of the pharmaceutical substances during transport and over prolonged periods of storage.

In a further aspect, the present invention provides a mixing syringe comprising the mixing device of the aforementioned aspect and a needle assembly comprising a needle. In a related aspect, the present invention also provides a mixing syringe comprising the mixing device of the aforementioned aspect and a connection component capable of connecting the mixing device to a needle assembly and/or a needleless access device, such as an intravenous delivery tube. Such connection component may utilize a number of known connection mechanisms, such as a luer connection, a luer lock connection, a screw-threaded connection, and the like.

In a preferred form, the mixing syringe is a retractable mixing syringe that comprises a retractable needle. Preferably, the delivery plunger is capable of engaging the retractable needle to thereby facilitate retraction of the needle. As utilized with reference to the retractable needle, the terms "engage" and "engaging" are intended to mean a range of connection mechanisms including, for example, contacting, interlocking, capturing, connecting, and the like. Suitably, retraction of the needle is facilitated by the biasing member of the combination plunger, such as a spring, elastic or other member capable of storing and releasing energy to facilitate needle retraction, as hereinbefore described. It will be appreciated that the retractable syringe may comprise any needle retraction mechanism that is operable with the combination plunger and/or mixing device disclosed herein. The needle assembly may include a retractable needle, wherein the retractable needle comprises a cannula and a needle body engageable by the plunger member. Preferably, a plunger seal is mounted to the plunger member and is capable of engaging said needle body. Preferably, the needle assembly may further comprise a needle seal that retains the retractable needle, wherein the cannula of the retractable needle passes through the needle seal to permit delivery of the mixed substances or mixture to a user, patient, or other recipient. Optionally, the needle assembly may further comprise a retainer to assist retention of the needle prior to retraction and an ejector which assists release of the needle. By way of example, needle assemblies, components thereof and needle retraction mechanisms may be as described in International Publication WO2006/119570, International Publication WO2006/108243, International Publication WO2009/003234, International Publication WO2011/075760 and International Publication WO2013/020170, and/or U.S. patent application Ser. No. 13/693,915, although without limitation thereto. Also, a screw-threaded and/or luer connection may be used to connect a needle assembly, whether or not a retraction needle assembly is utilized, such as in WO2011/057335, although without limitation thereto.

The combination plunger may be assembled, packaged, and transported as a separate component from the remainder of the mixing syringe. In at least one embodiment, the mixing device portion of the syringe may be assembled, sterilized, and/or filled as a separate component, and sealed with a sealing membrane for storage and/or transportation. The sealing membrane may be any type of sterile membrane such as a fabric seal, particularly a nonwoven fabric seal such as that sold under the trade name TYVEK, or any other type of sealing sterile membrane. The combination plunger device may then be attached to the mixing device to form a mixing syringe. The sealing membrane may be removed by the user or automatically removed or pierced by the delivery plunger during operation of the mixing syringe. In certain embodiments, the sealing membrane functions to maintain the sterility of the portion of the inner barrel between the plunger seal and the proximal end of the inner barrel, and may be removed or pierced just prior to, or during, operation of the mixing syringe.

In yet another aspect, the invention provides a method of assembling a combination plunger including the steps of:
   (a) releasably engaging a mixing plunger and a delivery plunger;
   (b) loading a biasing member into the mixing plunger;
   (c) energizing the biasing member in a pill housing; and
   (d) releasably engaging the pill housing to the mixing plunger to retain the biasing member in an initially energized state.

In a preferred embodiment, the method of assembling a combination plunger device include the additional step of inserting the combination plunger through a flange connector before step (b).

In a further aspect, the invention provides a method of manufacturing a mixing syringe comprising a combination plunger, the method including the steps of:
   (A) locating a first mixing substance in an outer chamber of the mixing syringe and inserting a first or proximal seal in the outer chamber of the mixing syringe in contact with the first mixing substance;
   (B) locating a second mixing substance in an inner chamber of the mixing syringe and inserting a plunger seal in the inner chamber;
   (C) aligning a delivery plunger of the combination plunger for axial translation within the inner barrel, wherein the delivery plunger is initially proximal to one or more apertures of the inner barrel and capable of connecting to the plunger seal; and
   (D) mounting a mixing plunger of the combination plunger in the outer chamber, wherein the mixing plunger contacts the first or proximal seal.

In an embodiment, the method of manufacturing the mixing syringe may include the further step of mounting the combination plunger device to the syringe by connection between a flange connector of the combination plunger device and a barrel extension of the syringe.

In one embodiment, the method may further comprise sealing the mixing syringe with a sealing membrane after step (B). Preferably, this embodiment includes the step of removing the sealing membrane prior to connecting the delivery plunger to the plunger seal, as contemplated by step (C), for drug delivery. The sealing membrane may be as hereinbefore described, such as the nonwoven membrane sold under the trade name TYVEK, although without limitation thereto.

In at least one embodiment, the method further includes, prior to step (A), inserting a distal seal in the outer chamber of the mixing syringe. In at least one embodiment, the method further includes, prior to step (A), affixing a vent cap comprising the one or more vents to a portion of the inner barrel that is located distally of the one or more apertures. Preferably, a distal end of the outer barrel is connected to the vent cap.

In further embodiments, the method further includes the step of inserting a needle assembly into the inner chamber located distally of the one or more apertures.

In a still further aspect, the invention provides a method of operating a syringe comprising a mixing device, said method including the steps of:
   (i) operating a mixing plunger of a combination plunger to thereby mix a plurality of substances in the mixing device;
   (ii) rotating a delivery plunger of the combination plunger to disengage it from the mixing plunger; and
   (iii) operating the delivery plunger of the combination plunger to deliver the substances mixed at step (i) to a recipient.

In at least one embodiment, the method further includes after step (iii), activating a needle retraction mechanism to retract the needle into the syringe. Preferably, the activation of the needle retraction mechanism occurs after substantially all of the substances are delivered to the recipient.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

Figure 1A:
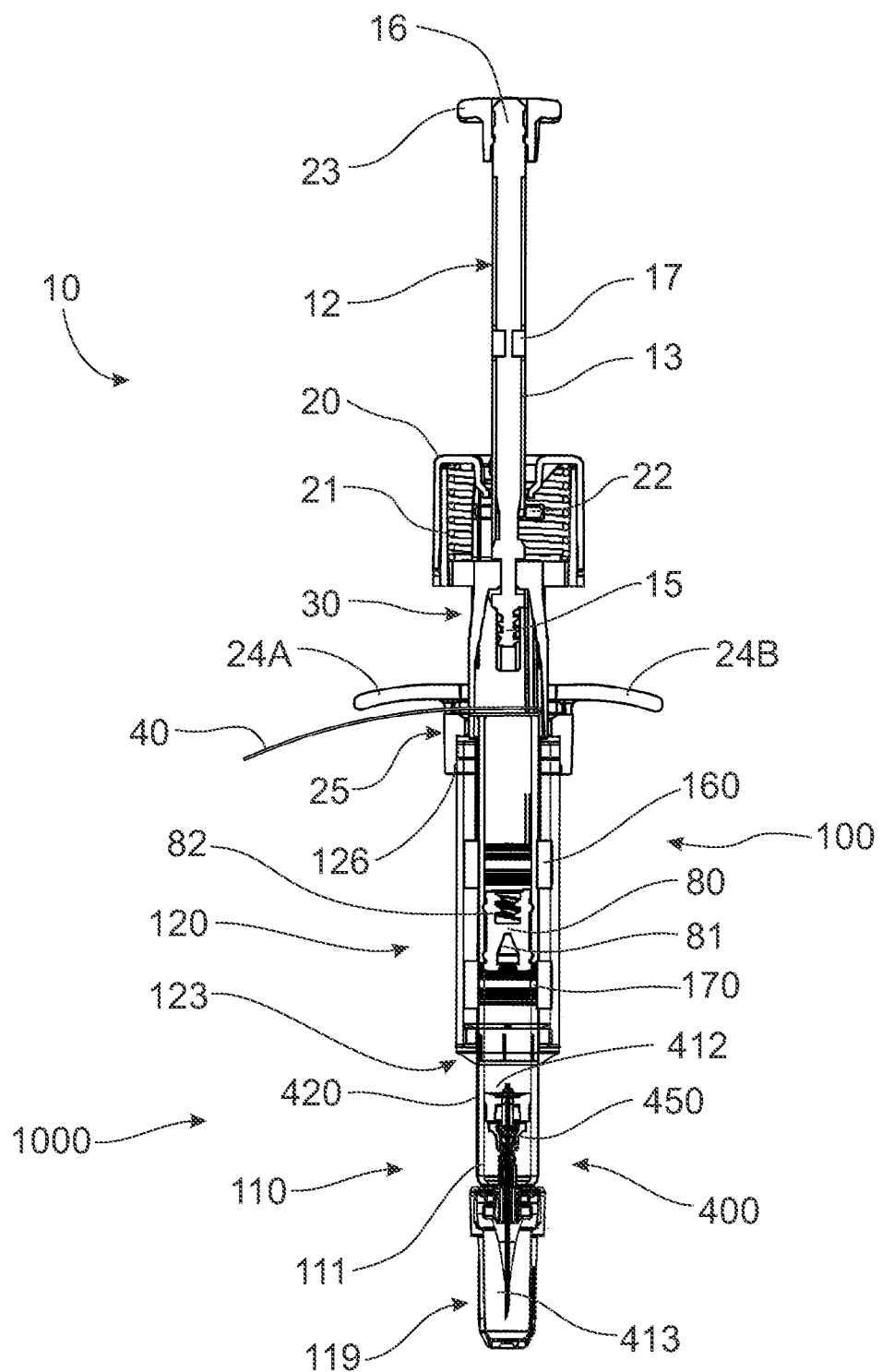
FIG. 1A shows an embodiment of a mixing syringe comprising a combination plunger device.
Figure 1B:
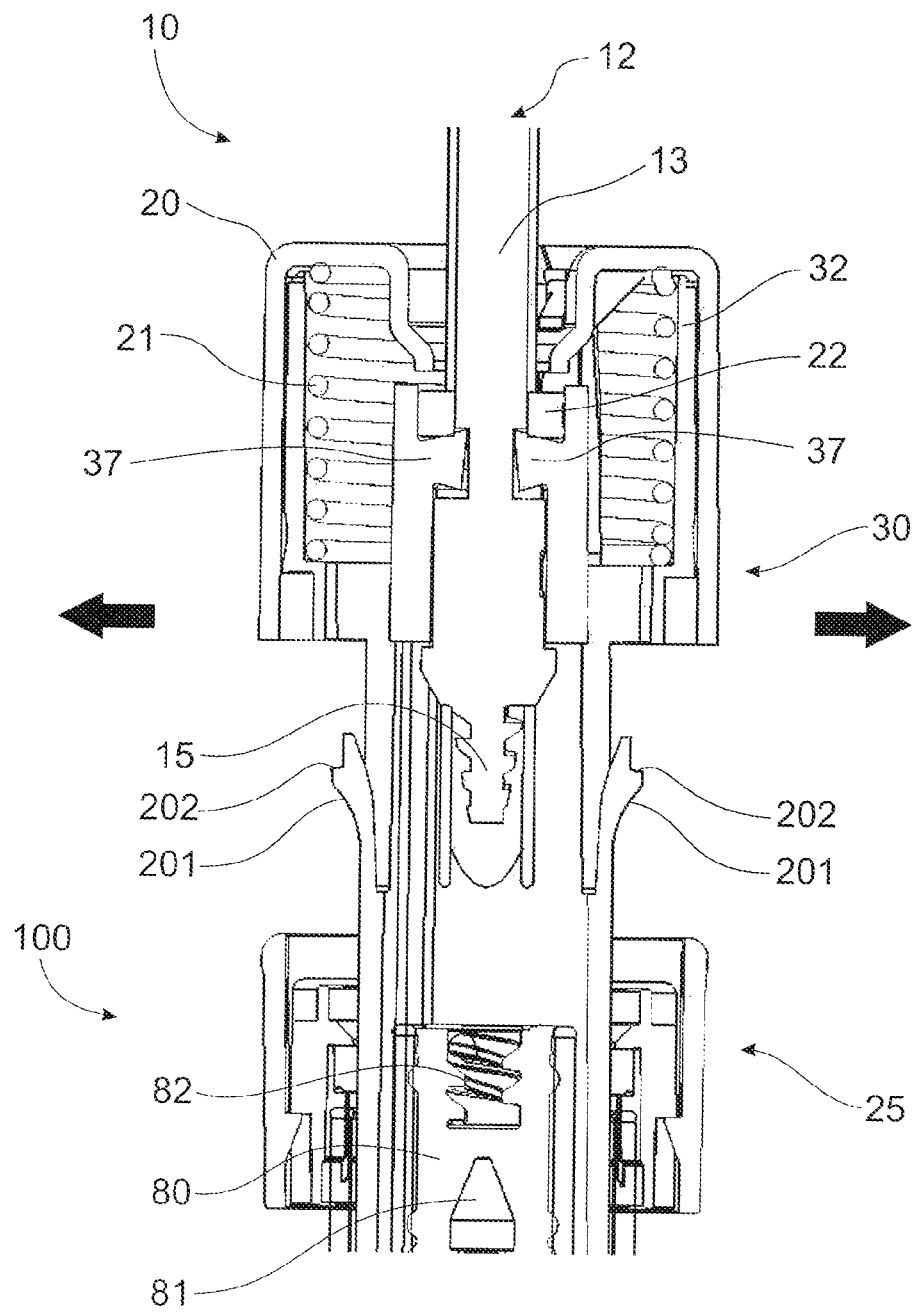
FIG. 1B shows an enlarged 90 degree rotated view of the embodiment of a mixing syringe comprising a combination plunger device shown in FIG. 1A.
Figure 2:
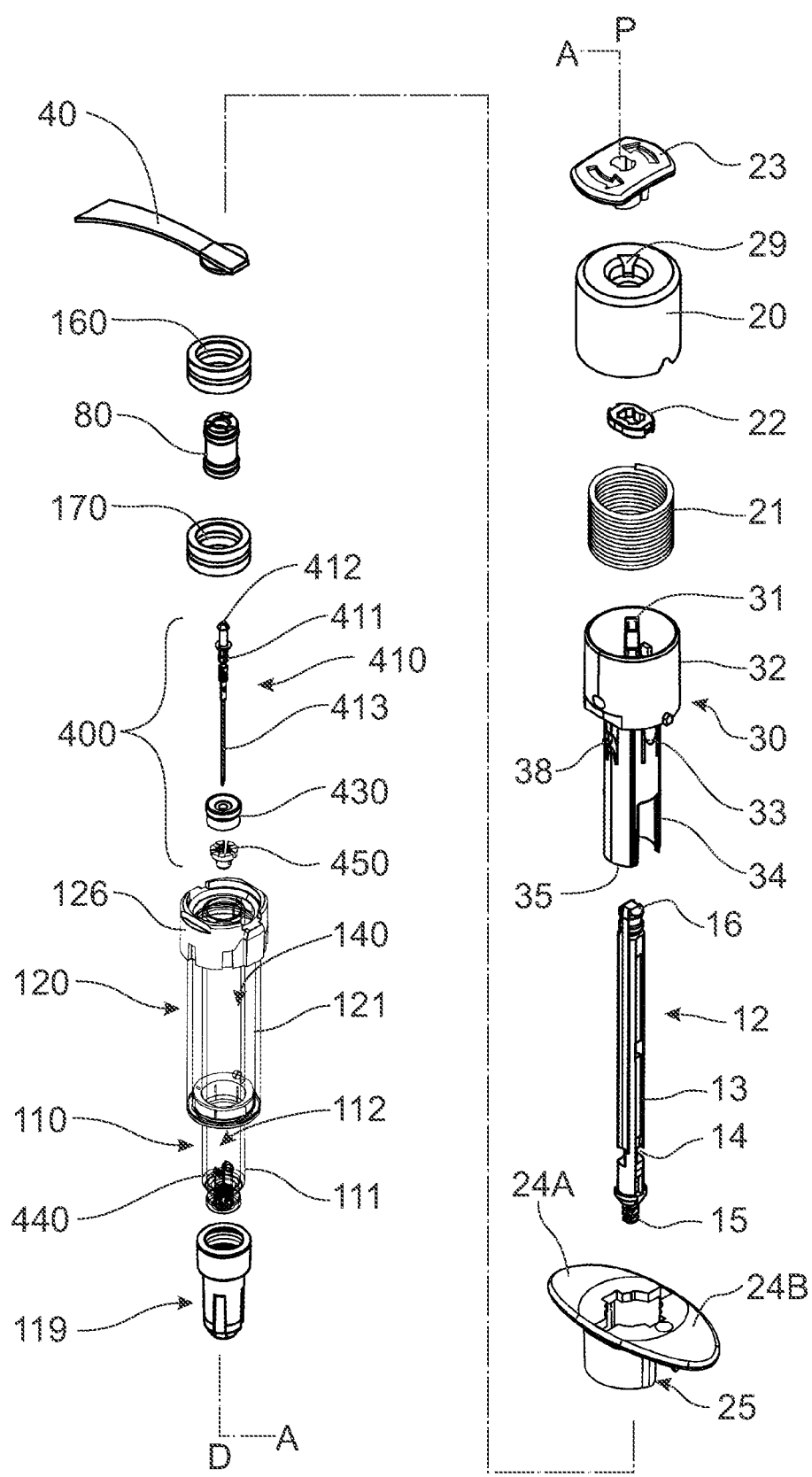
FIG. 2 shows an exploded view of an embodiment of a mixing syringe comprising a combination plunger device.

Referring to FIG. 1 and FIG. 2 an embodiment of mixing syringe 1000 comprises mixing device 100, combination plunger device 10 and retractable needle assembly 400. Mixing device 100 comprises inner barrel 110 comprising wall 111 and inner chamber 112, outer barrel 120 comprising wall 121, combination plunger device 10 and retractable needle assembly 400. Outer chamber 140 of mixing device 100 is formed between wall 111 of inner barrel 110 and wall 121 of outer barrel 120. Inner barrel 110 and outer barrel 120 may be made of any of a number of materials including plastics and glass, but are preferably made of glass. Inner barrel 110 and outer barrel 120 are in a substantially concentric relationship, such that inner barrel 110 and outer barrel 120 possess a substantially common, central longitudinal axis. Inner barrel 110 and outer barrel 120 are non-rotatable with respect to each other.

Combination plunger device 10 comprises delivery plunger 12, mixing plunger 30, biasing member 21, pill housing 20, cam clip 22 and flange connector 25. The flange connector 25 may be utilized to connect the combination plunger device 10 to the proximal end of the mixing device inner and/or outer barrels 110, 120 at barrel extension 126. Delivery plunger 12 comprises rod 13, lock-out recesses 17, connection recesses 14 and seal-engaging member 15, which in this embodiment is screw threaded and can engage complementary, screw-threaded recess 82 of plunger seal 80. Plunger seal 80 further comprises needle-engaging portion 81. Delivery plunger 12 further comprises proximal end 16 to which button 23 is releasably connected. Mixing plunger 30 comprises head 32 having flex members 31 and lock-out members 37, connection members 33 and shaft 34 which comprises distal end 35, and locking fingers 38. As shown in FIG. 1B, lock-out members 37 of mixing plunger 30 may at least initially engage the delivery plunger 12, for assembly, transportation, storage, or otherwise. During operation, mixing plunger 30 may be rotated, thereby rotating cam clip 22 which causes lock-out members 37 to be flexed or biased outwardly in the direction shown by the solid arrows by cam clip 22, thereby disengaging lock-out members 37 from delivery plunger 12. As described further herein, after release of pill housing 20, cam clip 22 will translate proximally to release lock-out members 37. The lock-out members 37 will be permitted to engage corresponding lock-out recesses 17 of the delivery plunger, to prevent delivery plunger 12 from moving distally after drug delivery and needle retraction. Cam clip 22 and lock-out members 37 may be configured to provide tactile and/or audible feedback to inform the user that the device has been locked-out. This provides a useful, optional, safety feature to the combination plunger device 10. Similarly, connection members 33 engage with connection recesses 14 of delivery plunger to prevent rotation of the delivery plunger 14 before the mixing stage is completed.

A sealing membrane 40 may initially reside at barrel extension 126 to cover the proximal end of the barrel(s) after assembly and filling with substance(s), but before connection with the combination plunger device 10. Alternatively, the sealing membrane may be attached to the proximal end of the inner barrel 110 and cover only inner chamber 112. The sealing membrane 40 may be any of a variety of sterile fabrics and materials, such as TYVEK, used in the medical devices and pharmaceuticals industry. The sealing membrane 40 may be removed automatically or by the mixing syringe user during operation.

Needle assembly 400 comprises retractable needle 410 comprising needle body 411 having plunger-engaging segment 412 and cannula 413 having fluid end 414, needle seal 430, retainer 440 (visible in FIG. 8) and ejector 450.

Combination plunger device 10 provides coordinated, synchronous axial movement of mixing plunger 30 and delivery plunger 12. Referring to FIGS. 1, 2 and 3A-C, mixing plunger 30 is axially, slidably movable in outer chamber 140 of outer barrel 120 of mixing device 100 of mixing syringe 1000 to thereby deliver the fluid contents of the outer chamber 140 to the inner chamber 112 via one or more apertures 114. Delivery plunger 12 is axially, slidably movable in inner chamber 112 of inner barrel 110 of mixing syringe 100 to engage screw-threaded recess 82 of plunger seal 80, and thereby axially, slidably move plunger seal 80 to deliver the fluid contents of the inner chamber 110 and subsequently engage retractable needle 410 for retraction thereof.

Typically, outer chamber 140 of mixing device 100 contains a liquid substance and inner chamber 112 contains a solid substance, whereby the liquid substance is mixable with the solid substance in the inner chamber 112 to form a mixed substance suitable for injection. In at least one embodiment, however, the outer chamber 140 and inner chamber 112 both contact liquid substances.

First or proximal seal 160 is in contact with distal end 35 of shaft 34 of mixing plunger 30. Second or distal seal 170 is positioned distally from proximal seal 160 within outer chamber 140. First or proximal seal 160 is axially, slidably moveable within outer chamber 140 by contact with and movement of the shaft 34 of mixing plunger 30. As may be best seen in FIG. 3B, apertures 114 on inner barrel wall 111 provide a fluid path that allows fluid from outer chamber 140 to flow into inner chamber 112. Initially, second or distal seal 170 is in sealing engagement with apertures 114 (e.g., covering apertures 114; compare FIG. 3A and FIG. 3B).

Outer barrel 120 further comprises vent cap 123 comprising plurality of vents 122, whereby vented space 142 is located between vents 122 and second or distal seal 170. Because the substances do not contact this vented space 142, vented space 142 may be unsterile and open to the atmosphere. This feature enables displacement of second or distal seal 170 towards plurality of vents 122 during the mixing step of operation, thereby opening one or more apertures 114 for passage of fluid from the outer chamber to the inner chamber. The fluid path from outer chamber 140 to inner chamber 112 remains sterile as a result of the displaced location of second or distal seal 170. The mixing syringe 100 further comprises a barrel extension (not visible) at its proximal end.

Figure 3A:
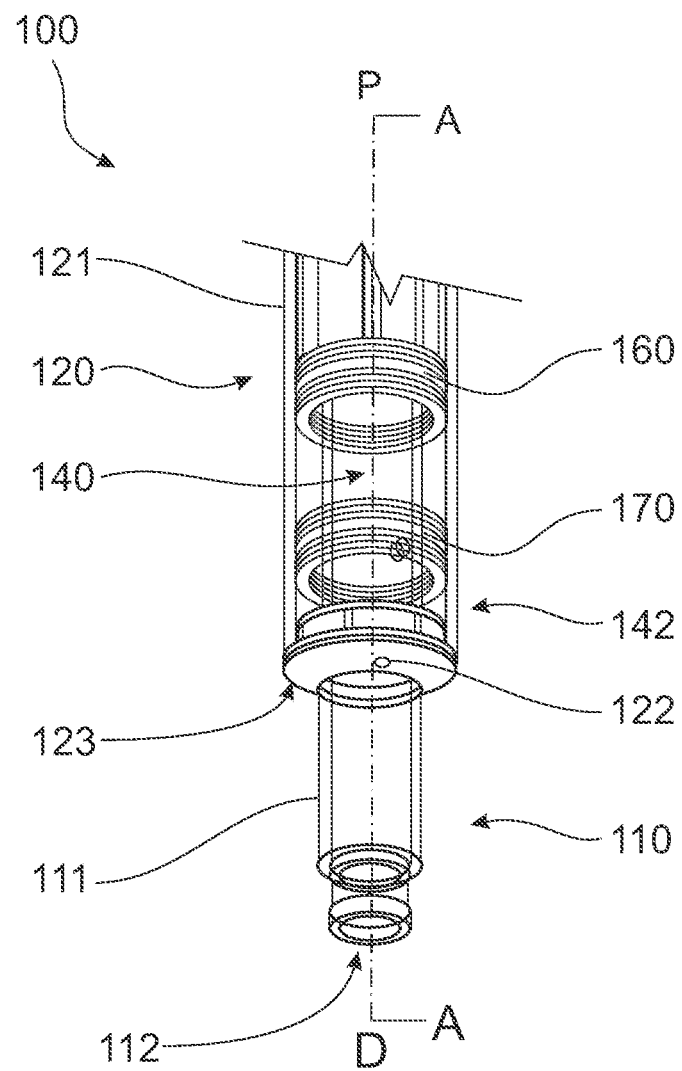
FIG. 3A shows an isometric view of an embodiment of a mixing syringe having a combination plunger device, according to one embodiment of the present invention.
Figure 3B:
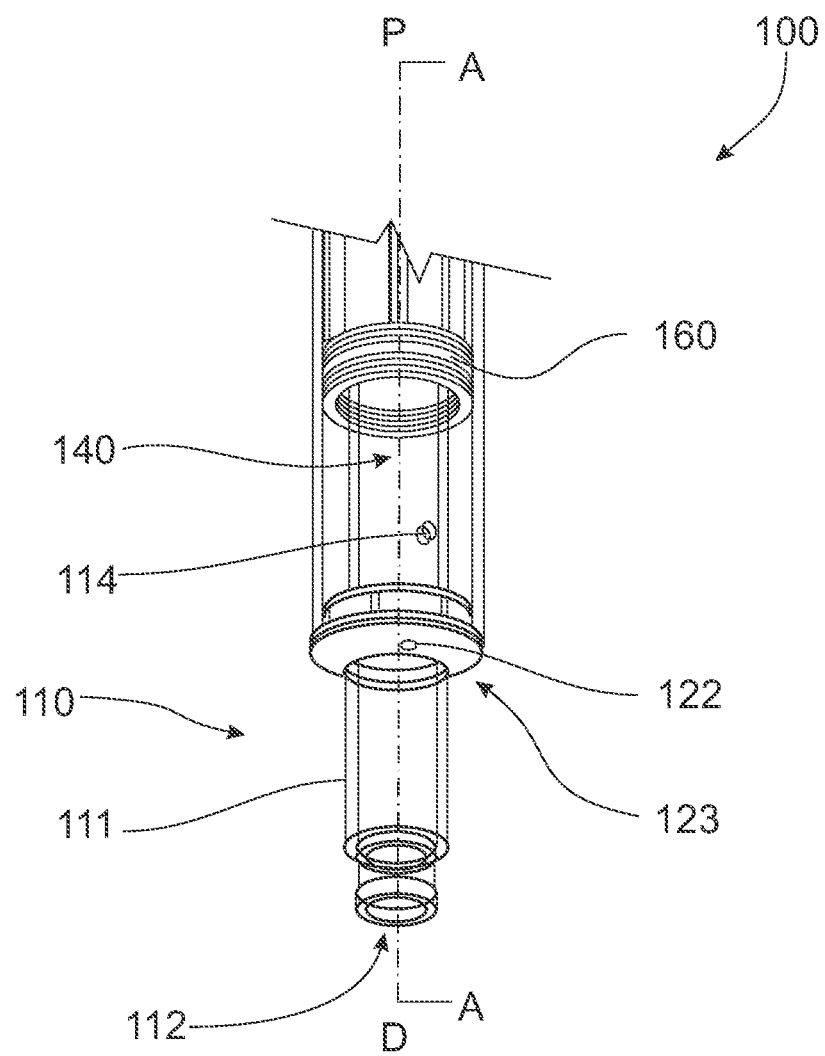
FIG. 3B shows an isometric view of the embodiment in FIG. 3A, without the distal seal to show the one or more apertures for passage of fluid.
Figure 3C:
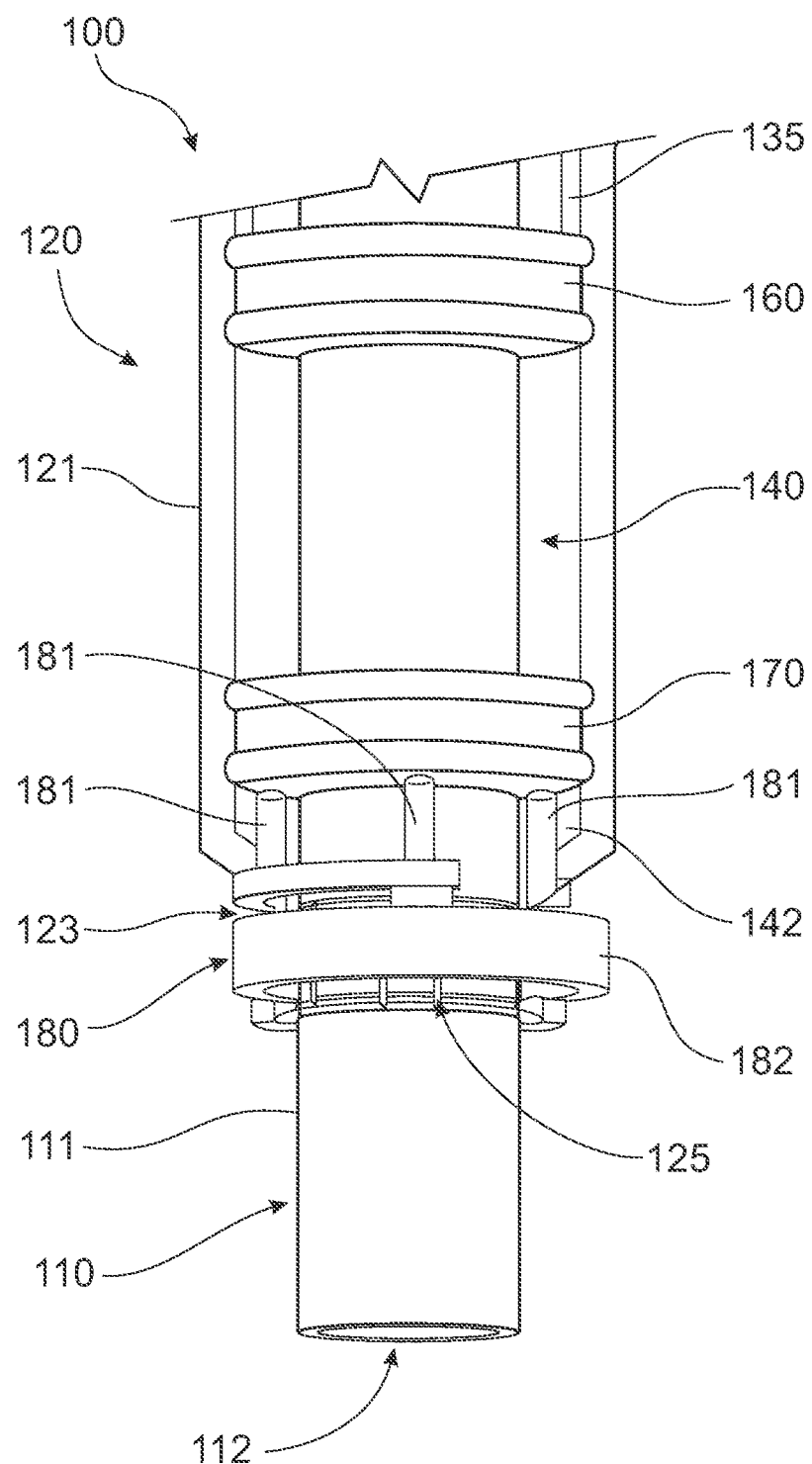
FIG. 3C shows an embodiment of a mixing syringe further comprising an optional safety cap mounted thereto.

In the embodiments shown in FIGS. 3A-C, outer barrel 120 is shorter than inner barrel 110. This configuration provides certain benefits such as, for example, allowing a heat transfer sleeve (not shown) to be placed around and in direct contact with a portion of inner barrel 110. This is useful to enable in situ lyophilization of a liquid substance located in inner chamber 112, by permitting filling with a liquid substance and then lyophilizing the liquid substance into a powder during or after manufacture of mixing syringe 100.

In other embodiments, inner barrel 110 and outer barrel 120 are of substantially similar length. This embodiment may be more aesthetically pleasing or provide additional volume by way of outer chamber 140. Also located in outer chamber 140 are first or proximal seal 160 and second or distal seal 170 slidably located therein.

In the embodiment shown in FIG. 3C, optional safety cap 180 is removably mounted to bracket 125 of outer barrel 120. Safety cap 180 comprises ring body 182 and protrusions 181 which are inserted through respective vents 122 (not visible in FIG. 3C) so as to be adjacent to, or in contact with, distal seal 170. This prevents undesired movement of distal seal 170, such as in response to air pressure changes during transportation or by inadvertent movement of mixing plunger 30 prior to intended activation by the user.

Figure 4:
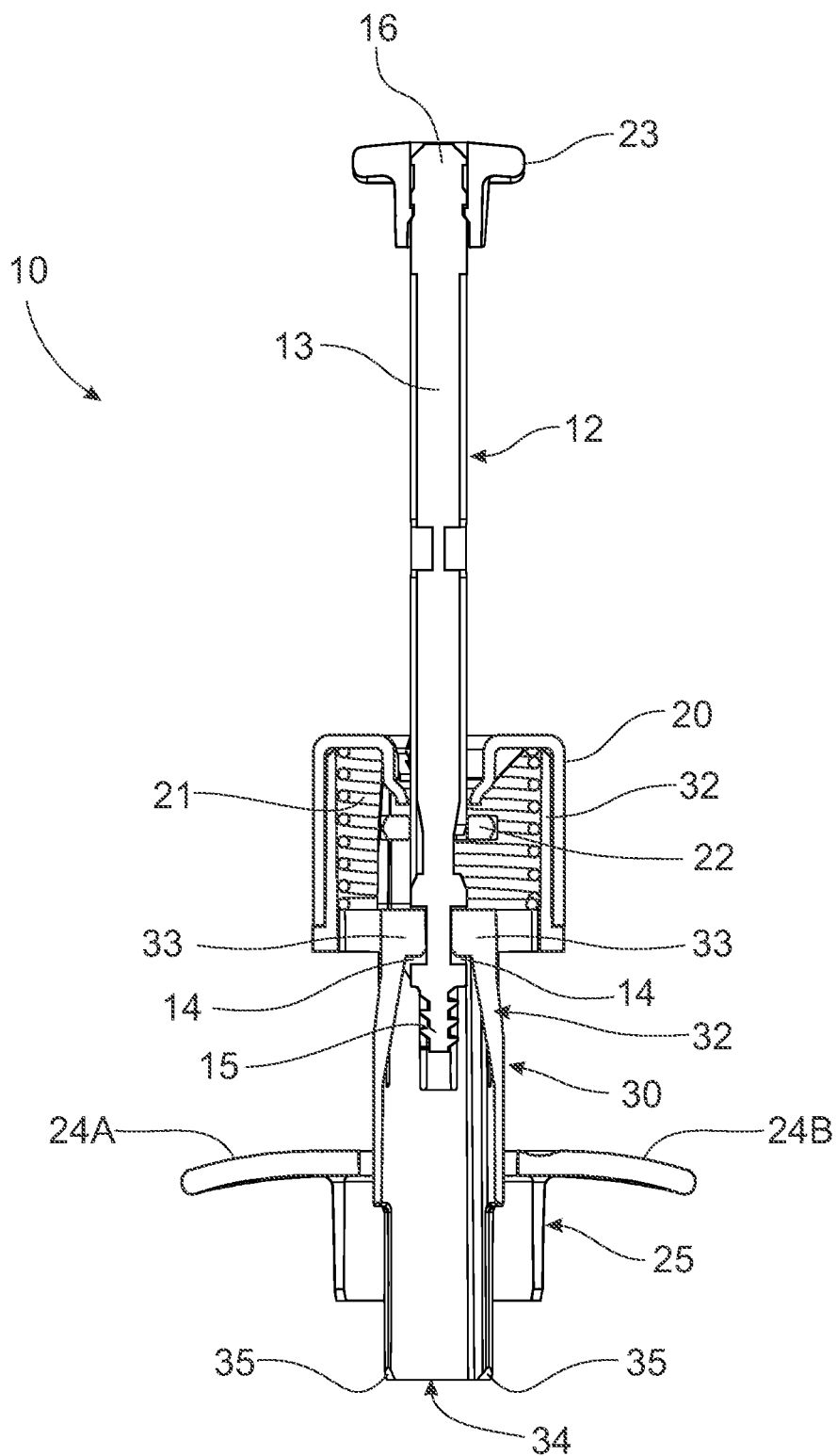
FIG. 4 shows a sectional view of a combination plunger device.
Figure 5:
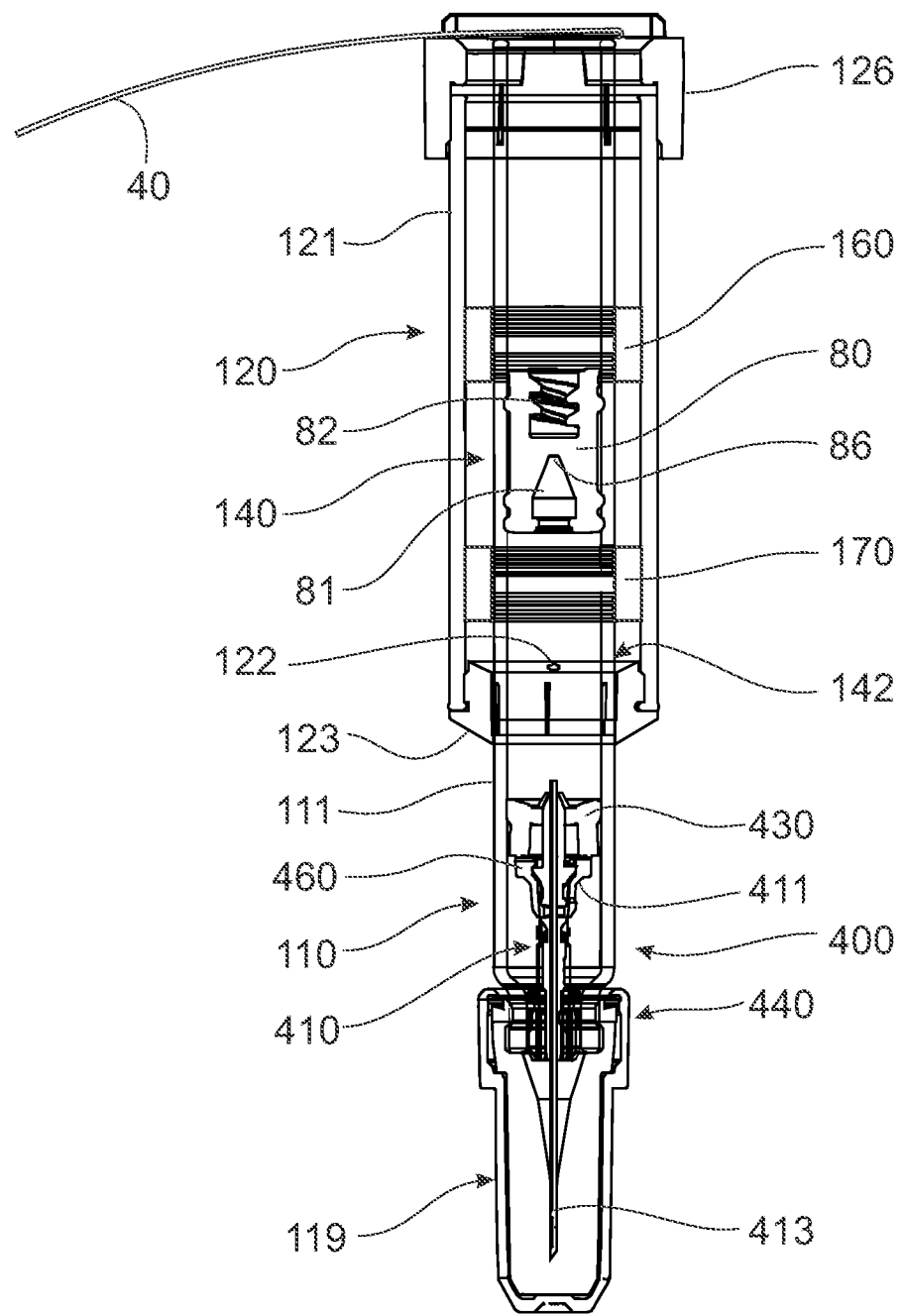
FIG. 5 shows a sectional view of a mixing device to which the combination plunger device shown in FIG. 4 may be connected to form a mixing syringe.
Figure 6A:
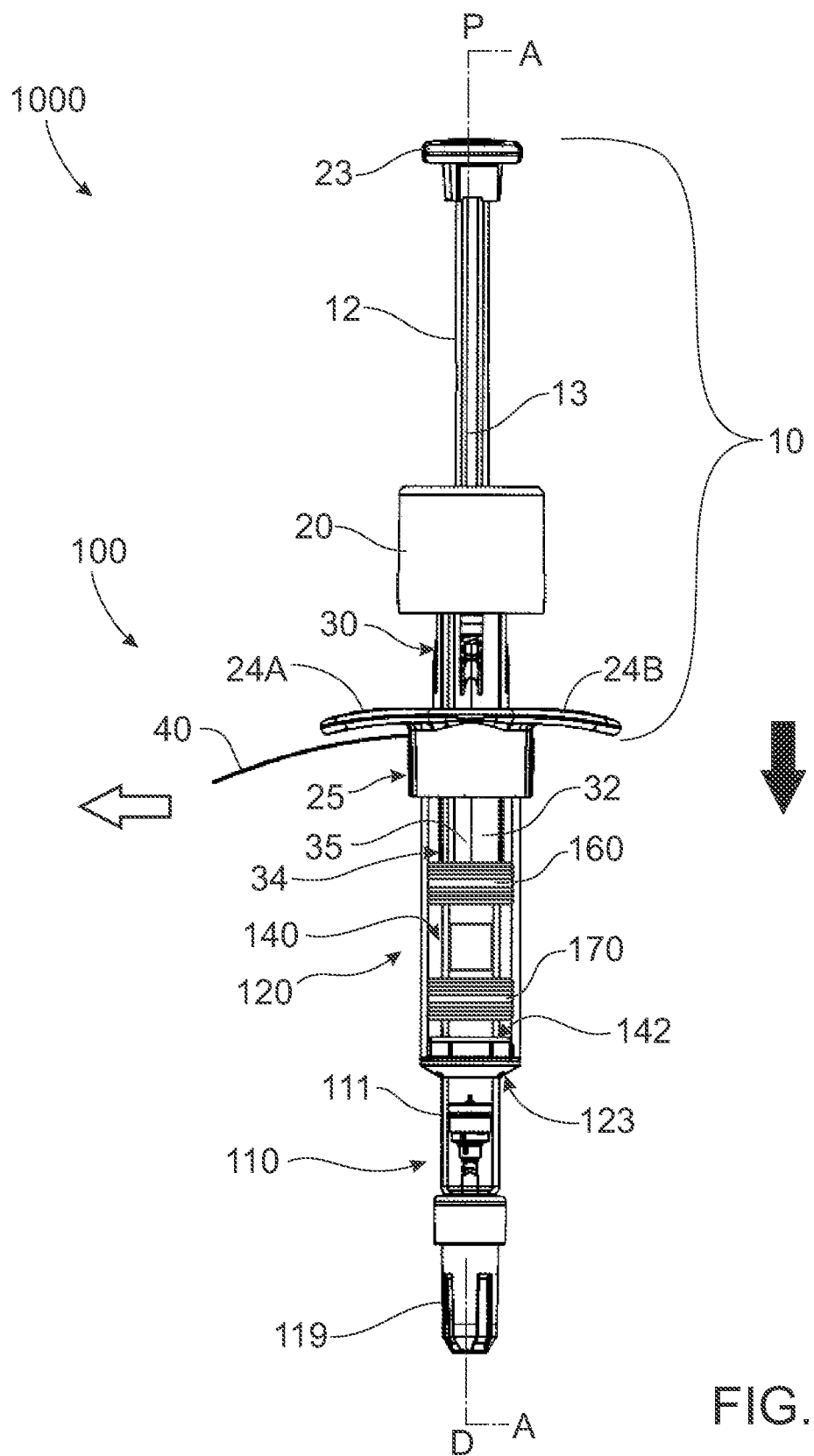
FIG. 6A shows an embodiment of a mixing syringe comprising a combination plunger device after filling and assembly.

The combination plunger device 10, as shown in FIG. 4, may be separately assembled from the remainder of the mixing syringe 100, as shown in FIG. 5. This may be desirable where, for example, a pharmaceutical company wishes to fill the syringe with the drug substance(s) in their standard fill-finish lines, and seal and ship such filled components to a separate company for final assembly. Similarly, this may be desirable for shipping, transportation, or a number of other reasons. Combination plunger device further includes connection recesses 14 on delivery plunger 12. The corresponding connection members 33 of the mixing plunger 30 may releasably connect to the delivery plunger 12 by engaging connection recesses 14 to form a unified combination plunger 10. Upon assembly, combination plunger 10 may be mounted to the remainder of mixing syringe 1000, as shown in FIG. 6A. As stated above, the sealing membrane 40 may be removed by the user or automatically during operation of the mixing syringe. Accordingly, in the embodiments evident in FIGS. 1, 4, 6A and 7A, plunger seal 80 may be, and in at least one embodiment is preferred to be, provided separately from combination plunger 10. In such configurations, delivery plunger 12 is connected to plunger seal 80 after combination plunger 10 is fitted into mixing device 100. This connection may utilize one or more known connection types, including screw-threaded connection, piercing connection, snap-fit connection, and the like, as would be readily appreciated by an ordinarily skilled artisan.

Operation of mixing syringe 100 will be described with particular reference to FIGS. 6A-6E and 7A-7E. In these embodiments, outer chamber 140 contains a fluid substance and inner chamber 112 contains a solid substance, whereby the fluid is mixable with the solid substance in the inner chamber 112 to form a mixed, fluid substance suitable for injection. As evident in FIG. 6A, optional safety cap 180 (shown in FIG. 3C) has been removed from outer barrel 120 to allow movement of second or distal seal in outer chamber 140.

Figure 6B:
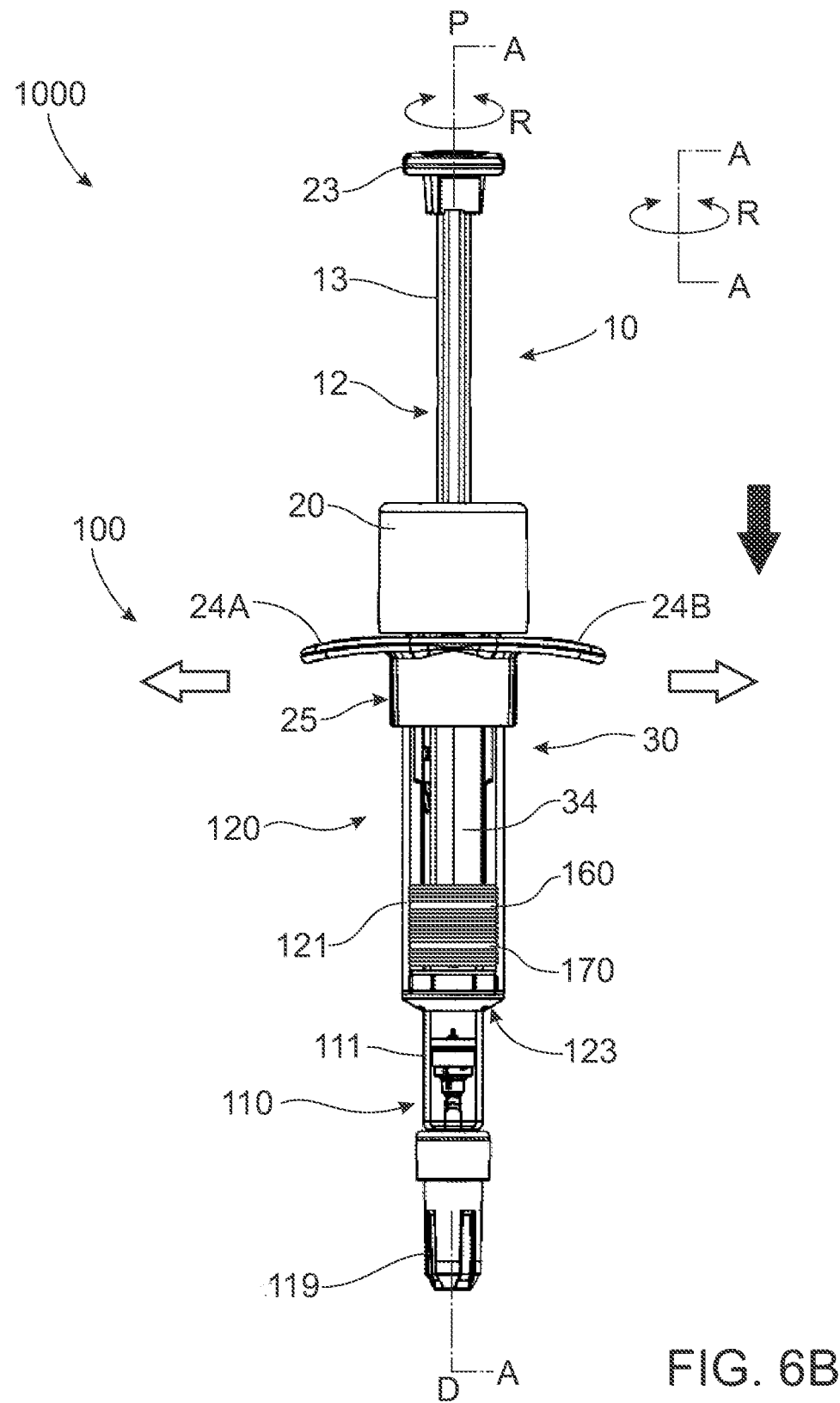
FIG. 6B shows an embodiment of a mixing syringe comprising a combination plunger device after initial depression of the combination plunger device to promote mixing via the mixing plunger of the mixing syringe.

Initially, second or distal seal 170 covers apertures 114 in inner barrel wall 111 to prevent movement of liquid from outer chamber 140 into inner chamber 112. Depression (i.e., axial movement towards needle 400 in the direction of the solid arrow) of combination plunger 10 at button 23 and/or delivery plunger 12 causes mixing plunger 30 to travel axially in the direction of the solid arrow. Thus depression of delivery plunger 12 causes coordinated, synchronous depression of mixing plunger 30. This forces first or proximal seal 160 distally in outer chamber 140 which forces liquid contained in outer chamber 140 to displace second or distal seal 170 (i.e., towards retractable needle 400), thereby opening apertures 114 to permit fluid to transfer from outer chamber 140 to inner chamber 112. Specifically, depression of mixing plunger 30 causes distal end 35 of shaft 34 to contact and push upon first or proximal seal 160 distally in the outer chamber 140. As shown in FIG. 6B, continued depression of mixing plunger 30 in the direction of the solid arrow forces further distal movement of first or proximal seal 160 within outer chamber 140, forcing continued fluid flow from outer chamber 140 to inner chamber 112, until first or proximal seal 160 is in contact with second or distal seal 170. Seals 160 and 170 may be caused to reach end of travel within outer chamber 140, where second or distal seal 170 will contact with vent cap 123. In this position, either seal 160 is in sealing engagement (i.e., covering) with apertures 114 or both seals 160 and 170 may be in partial sealing engagement with apertures 114. The latter is possible, for example, when fluid flow from outer chamber 140 to inner chamber 112 does not require the second or distal seal 170 to fully uncover the apertures 114.

At this point, fluid delivery from outer chamber 140 to inner chamber 112 is complete. As described in International Publication WO2013/020170, mixing plunger 30 may comprise locking prongs or fingers which are outwardly biased and would engage an inner lip or tabs of barrel extension 126 to form a locking system that prevents proximal movement (i.e., towards a user) of mixing plunger 30 beyond this point. For example, this locking system ensures that mixing plunger 30 cannot be withdrawn from outer chamber 140. Locking mixing plunger 30 after mixing may be useful in directing the force of delivery plunger 12 through needle 410 to inject the liquid substance, instead of forcing the liquid substance back into outer chamber 140. This may also be achieved by the final positioning of first or proximal seal 160 in sealing engagement with apertures 114. Similarly, full axial movement of mixing plunger 30 and/or engagement between mixing plunger 30 and one or more detent aspects of outer barrel 120 may unlock delivery plunger 12 or a locking aspect of inner barrel 110 to enable axial depression of delivery plunger. This provides useful user feedback to ensure that the proper injection procedures are followed with the device and that reconstitution or mixing of the drug treatment(s) is enabled prior to injection into the patient. An embodiment of a locking system will be described hereinafter.

It will be appreciated that venting space 142 between the second or distal seal 170 and vents 122 is never in contact with any substance(s) in mixing device 100, hence there is no need to maintain sterility in the area of the venting space 142. Venting space 142 may fill with air, which is displaced out of the annular space between outer barrel 120 and inner barrel 110 and between vents 122 and the second or distal seal 170 upon depression of mixing plunger 30 and axial movement of second or distal seal 170. Furthermore, because second or distal seal 170 initially covers apertures 114 in wall 111 of inner barrel 110, sterility of this fluid path between outer chamber 140 and inner chamber 112 is maintained during use of mixing device 100. Only second or distal seal 170 is potentially in contact with any non-sterile portion of outer barrel 120 and inner barrel 110, as fluid is caused to flow from outer chamber 140 into inner chamber 112 without ever contacting the non-sterile portion.

It will also be appreciated that, in at least one embodiment of the present invention, the retractable mixing syringe 100 is a "closed system," meaning there is no venting of the fluid path other than by needle injection. Upon completion of mixing of substances in inner chamber 112, syringe 100 is ready to use. Rigid needle shield 119 is removed, cannula 413 of needle 410 is inserted into a recipient and delivery plunger 12 is depressed to deliver the mixed, fluid contents of inner chamber 112 to the recipient. Standard medical practices, such as manual agitation of the syringe to further facilitate mixing of the substances and/or priming the syringe to remove any residual air prior to injection, may be performed prior to needle insertion and injection of fluid contents.

Figure 6C:
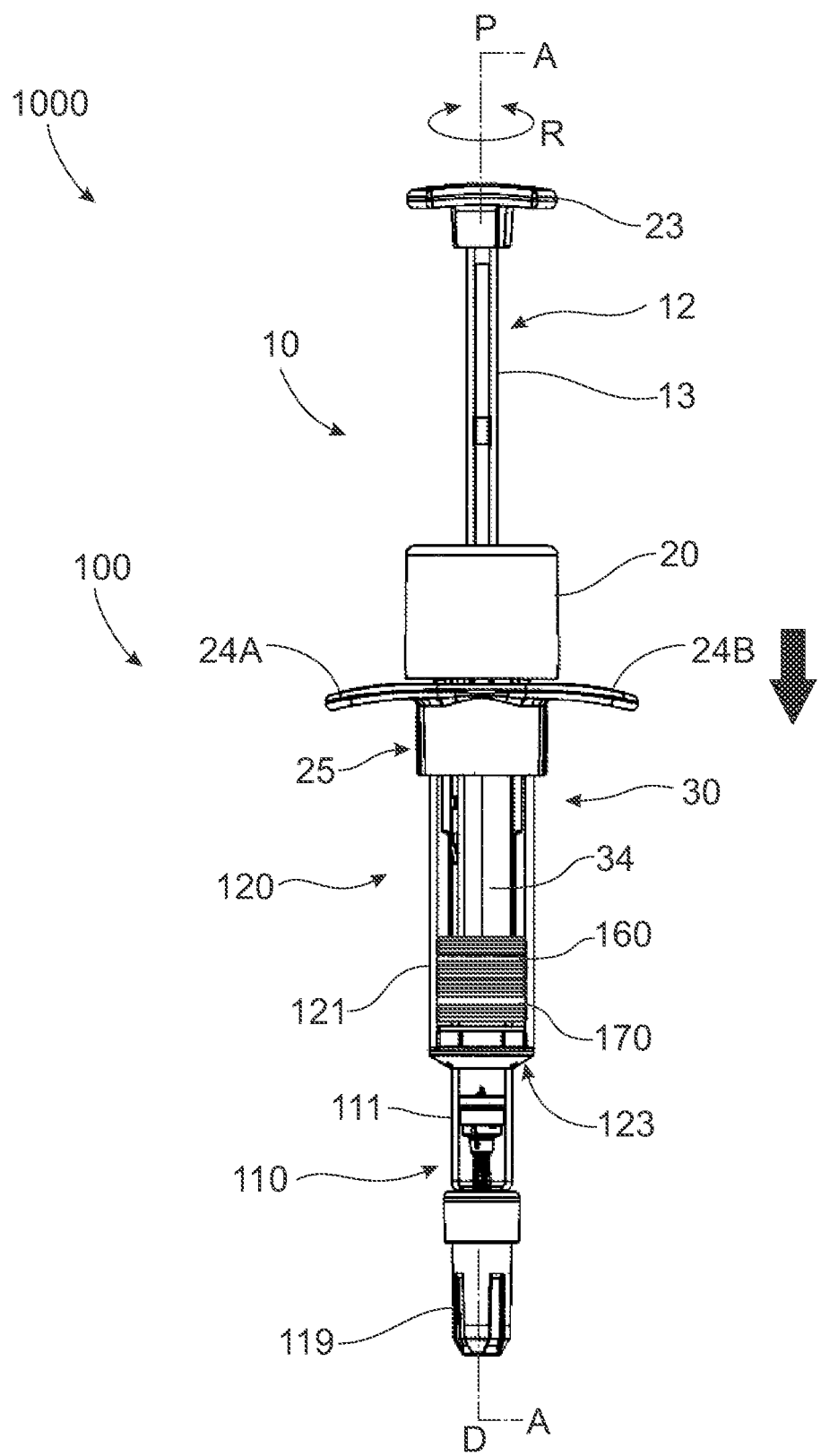
FIG. 6C shows an embodiment of a mixing syringe comprising a combination plunger device after rotation of the delivery plunger to permit injection.
Figure 7A:
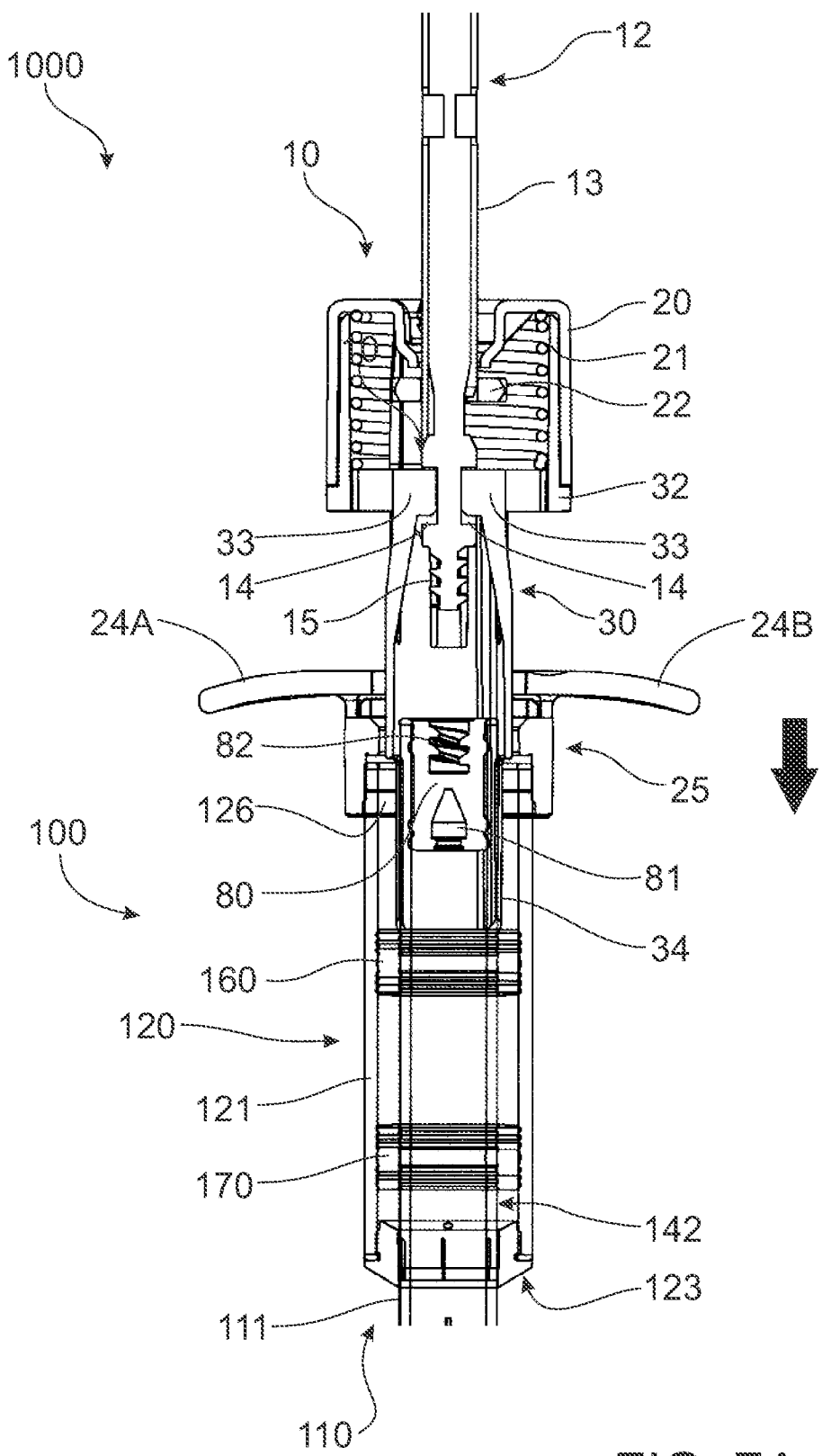
FIG. 7A shows an enlarged sectional view of a mixing syringe comprising a combination plunger device after filling and assembly.
Figure 7B:
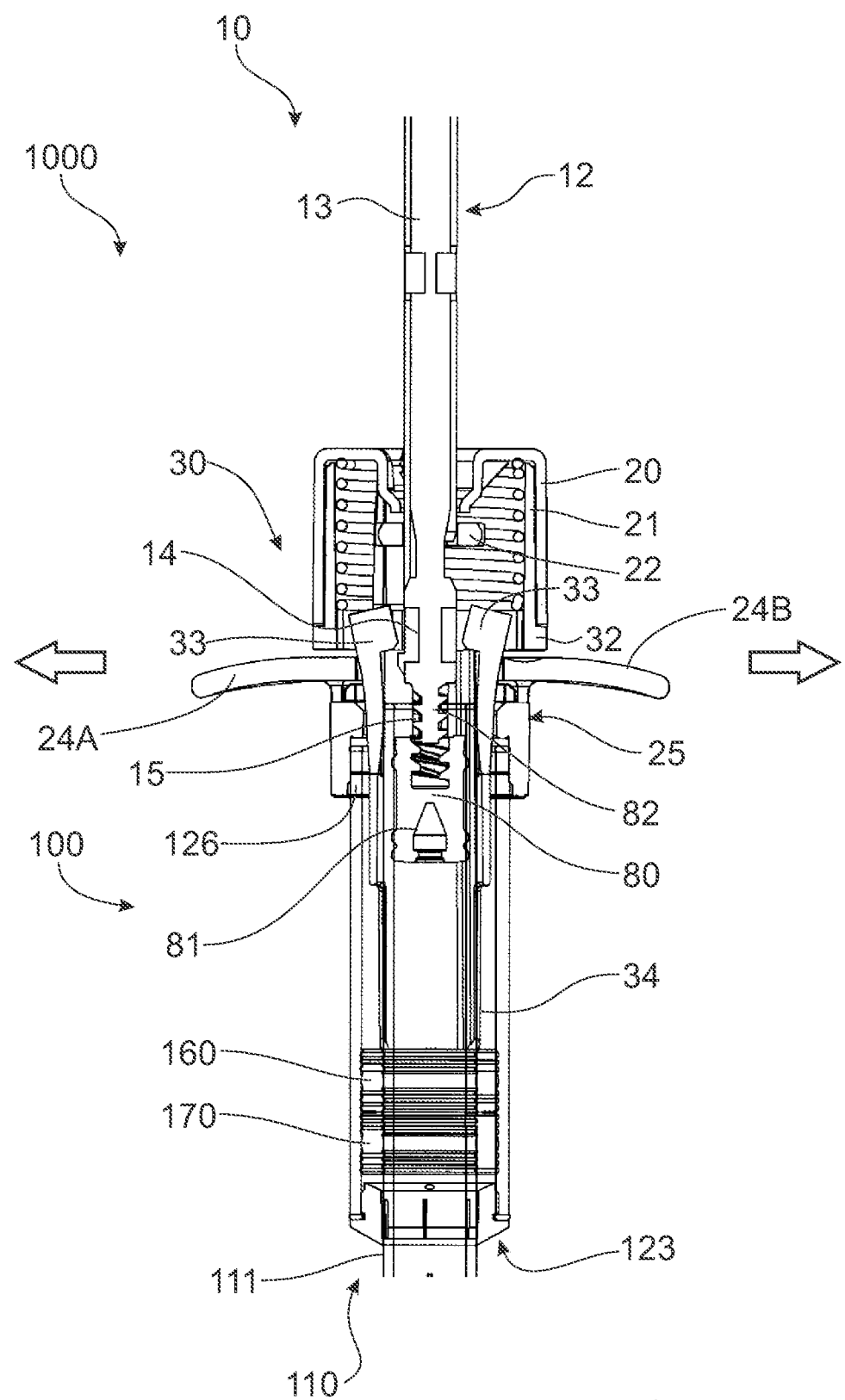
FIG. 7B shows an enlarged sectional view of a mixing syringe comprising a combination plunger device after initial depression of the combination plunger device to promote mixing via the mixing plunger of the mixing syringe.
Figure 7C:
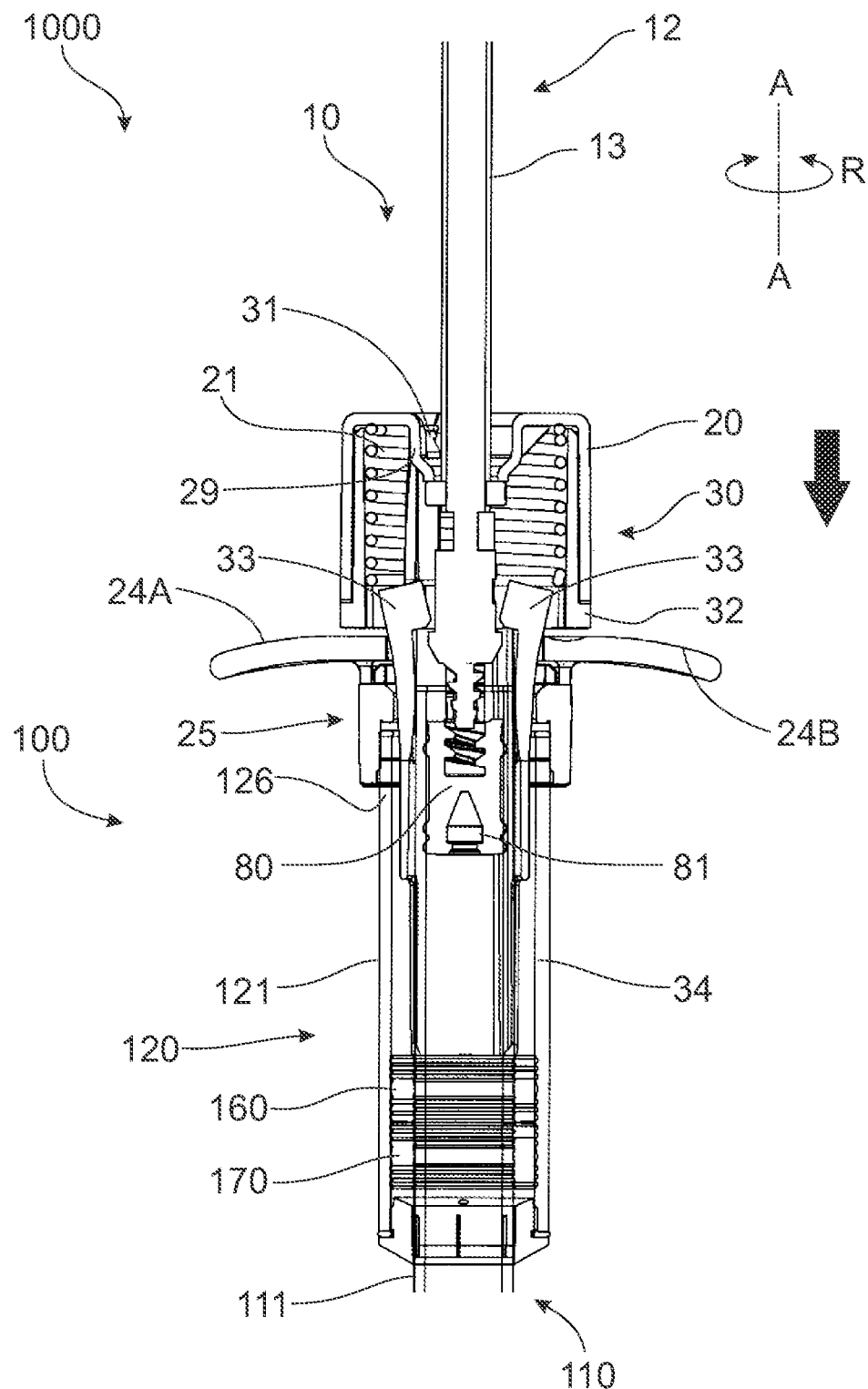
FIG. 7C shows an enlarged sectional view of a mixing syringe comprising a combination plunger device after rotation of the delivery plunger to permit injection.

The combination plunger device 10 of the present invention permits the user to drive the action of the syringe by manipulating only one plunger (i.e., depression of only delivery plunger 12). Initially, delivery plunger 12 and mixing plunger 30 are connected, as described herein, such that axial motion of delivery plunger 12 causes coordinated, related motion of mixing plunger 30. After the mixing stage is complete, one or more of the plunger 12 and 30 may be manipulated to disengage from the other. For example, in at least one embodiment, connection members 33 permit the delivery plunger 12 to be rotated after the mixing stage has completed to disengage the delivery plunger 12 from the mixing plunger 30. For example, mixing plunger 30 may have connection members 33 which releasably engage corresponding connection recesses 14 of delivery plunger 12. Connection members 33 are caused to disengage from connection recesses 14 as the mixing stage is performed and completed. In one embodiment, connection members 33 are caused to disengage from connection recesses 14 by contact between the connection members 14 and the proximal end of outer barrel 120 which forces the connection members 33 outwards (i.e., in the direction of hollow arrows in FIGS. 6B and 7B). After disengagement, further manipulation of the delivery plunger 12, such as axial translation in the distal direction, may occur regardless and separate from the position or manipulation of the mixing plunger 30. At the end of the stage shown in FIGS. 6B and 7B, the delivery plunger 12 may be rotated around axis A to disengage it from mixing plunger 30. Upon such disengagement, delivery plunger 12 and optional button 23 are permitted to be rotated around axis A, as shown in FIGS. 6C and 7C.

Figure 6D:
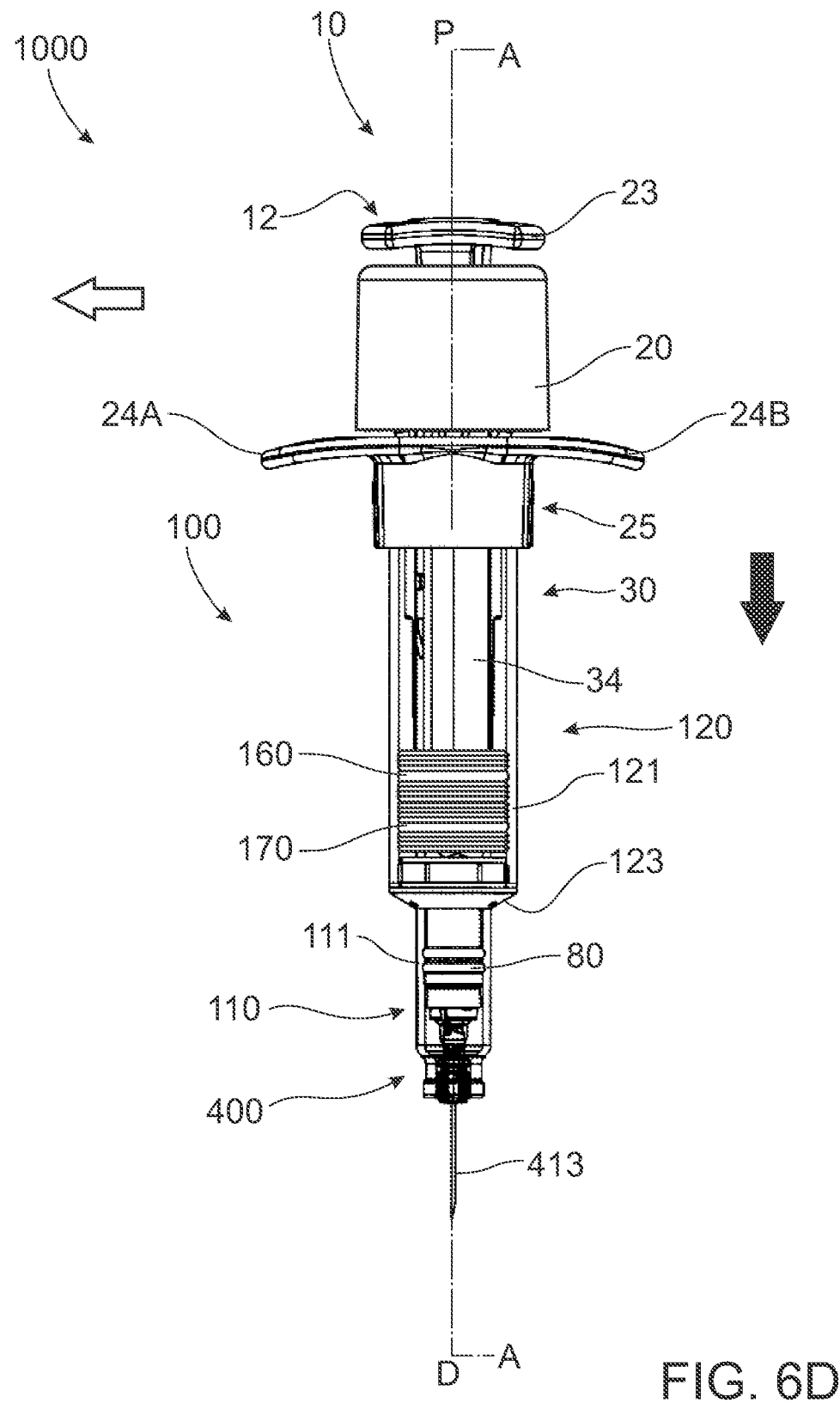
FIG. 6D shows an embodiment of a mixing syringe comprising a combination plunger device after further depression of the combination plunger device to promote drug delivery via the delivery plunger of the mixing syringe.
Figure 7D:
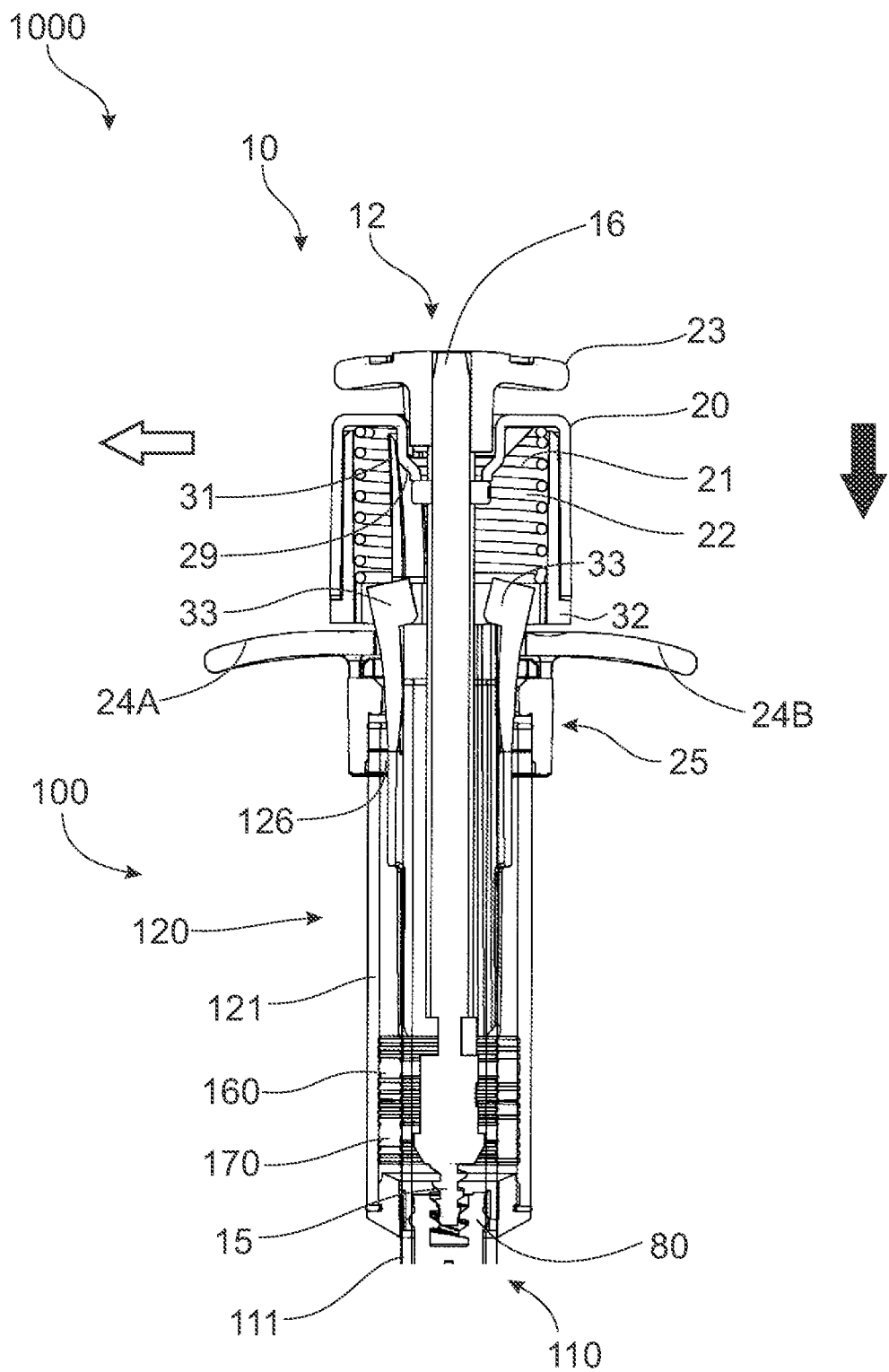
FIG. 7D shows an enlarged sectional view of a mixing syringe comprising a combination plunger device after further depression of the combination plunger device to promote drug delivery via the delivery plunger of the mixing syringe.

After the mixing stage has completed, the delivery plunger 12 of the combination plunger device 10 may continue to be depressed by the user to deliver the drug dose to the patient. Ideally, the mixing stage occurs before injection into the patient. After mixing and rotation of the delivery plunger 12 as described above, the syringe 1000 may be used for injection into the patient for drug dose delivery via depression of the delivery plunger 12. This is shown in FIGS. 6D and 7D as a motion in the direction of the solid arrow.

Figure 8:
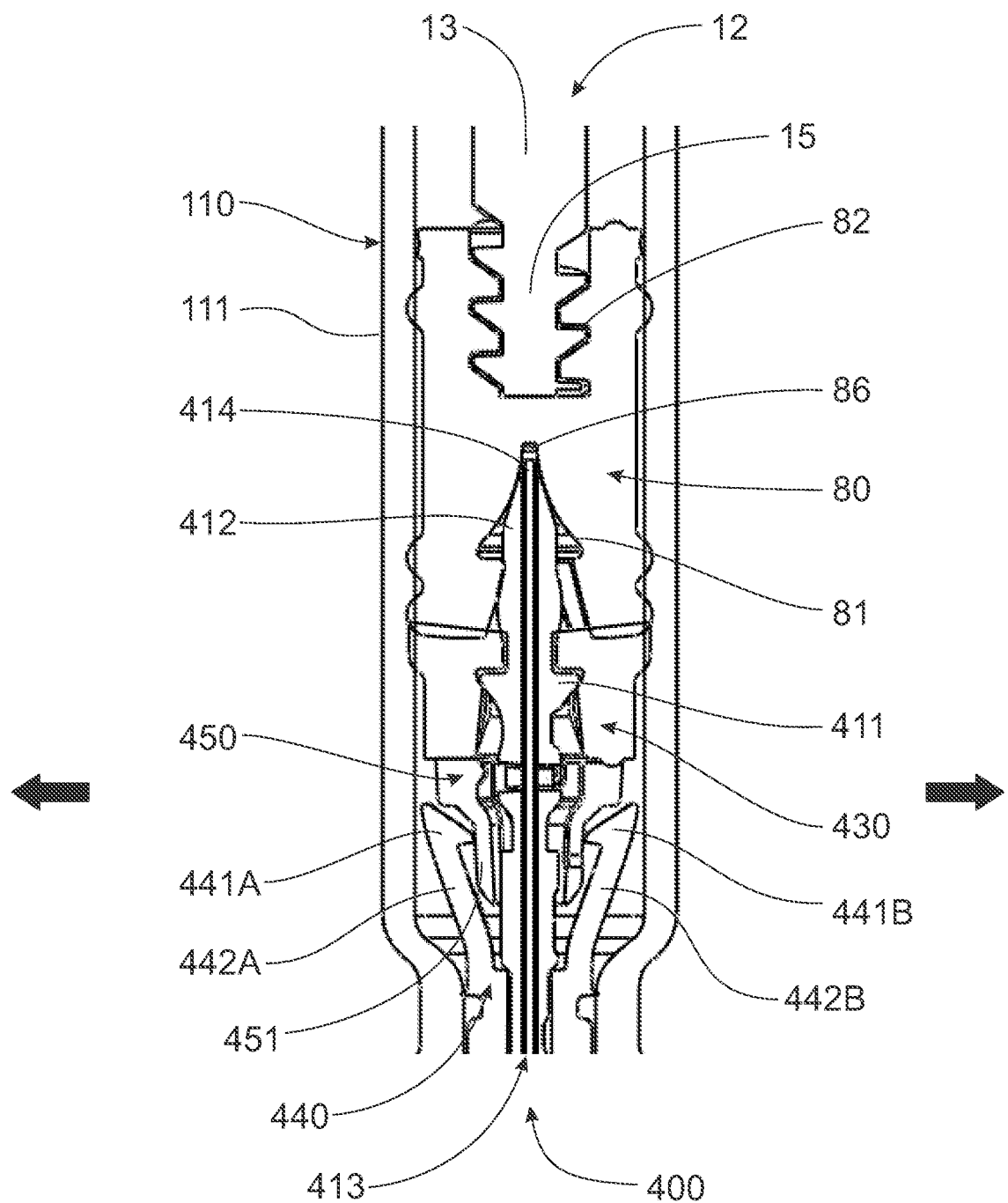
FIG. 8 shows an embodiment of a needle assembly engaged by a delivery plunger prior to retraction.

In at least one embodiment of the present invention, the combination plunger device 10 is utilized with a retractable mixing syringe 1000 having a needle retraction mechanism. In at least one embodiment of the present invention, the needle retraction is essentially similar to that described in WO2011/075760 and WO2013/0210170. During delivery of fluid contents, delivery plunger 12 moves axially through inner chamber 110 in the direction of the solid arrow in FIGS. 6D and 7D. As shown in FIG. 8, plunger seal 80 bears against needle seal 430, which in turn bears against ejector 450. Further to this, ejector ring 451 moves hook-ends 442A, B of arms 441A, B of retainer 440 radially outwardly in the direction of the solid arrows in FIG. 8, thereby disengaging needle body 411 from retainer 440 to release retractable needle 410 for subsequent retraction. At this point, recessed seat 81 of plunger seal 80 has engaged plunger-engaging segment 412 of retractable needle body 411, wherein proximal end 414 of cannula 413 is received by recess 86. This effectively couples retractable needle 410 to delivery plunger 12.

Figure 6E:
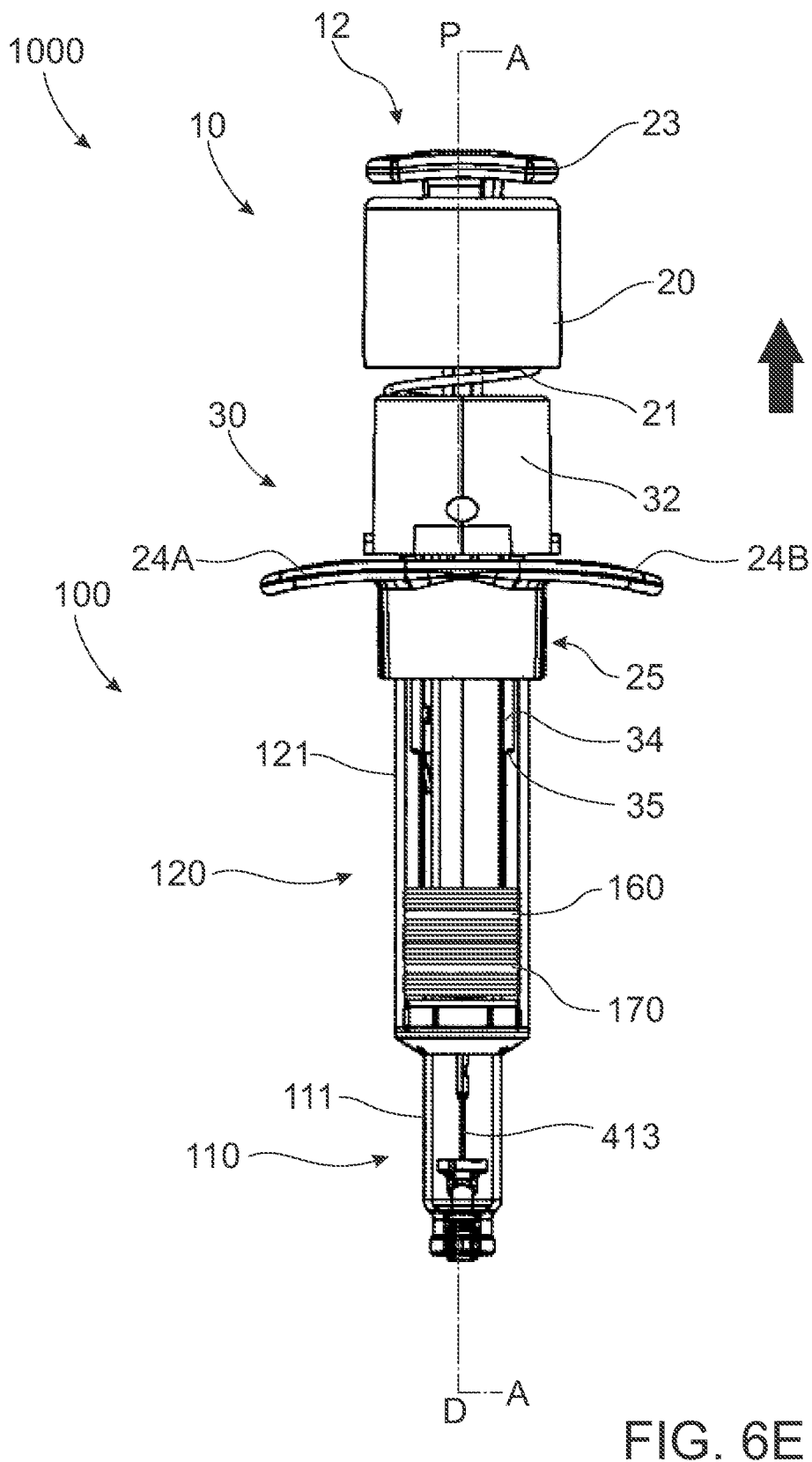
FIG. 6E shows an embodiment of a mixing syringe comprising a combination plunger device, wherein the mixing syringe is a retractable mixing syringe, after initiation of the retraction mechanism and retraction of the needle into the syringe.
Figure 7E:
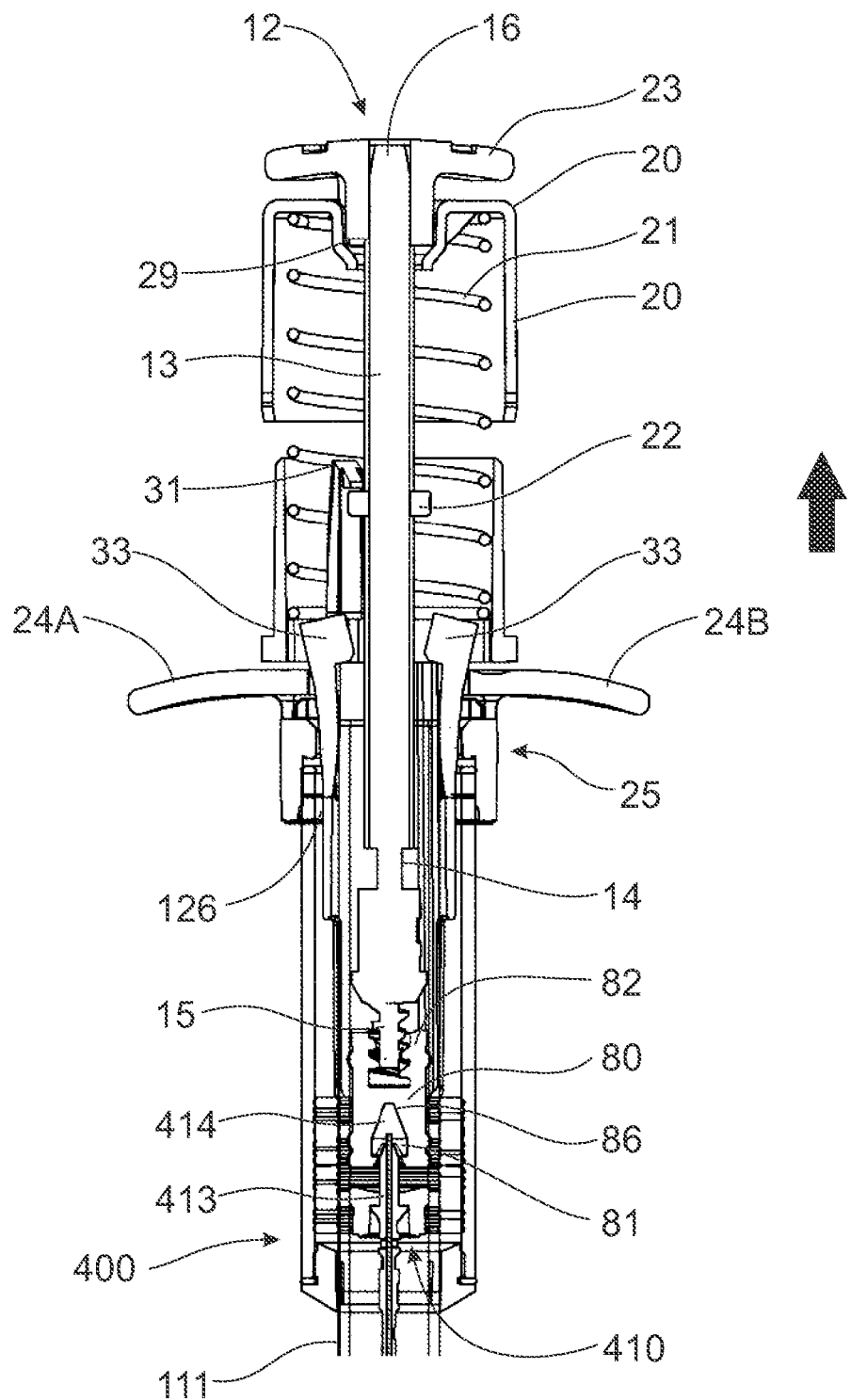
FIG. 7E shows an enlarged sectional view of a mixing syringe comprising a combination plunger device, wherein the mixing syringe is a retractable mixing syringe, after initiation of the retraction mechanism and retraction of the needle into the syringe.

As shown in FIGS. 6E and 7E, in order for retractable needle 410 to retract at the end of delivery of fluid contents, spring 21 must decompress from its energized state held in a compressed, energized state between head 32 of mixing plunger 30 and pill housing 20. These components are held in releasable engagement by flex member 31 connecting into pill housing 20 at locking window 29. Disengagement of these components is facilitated by proximal end 16 of delivery plunger 12 and/or button 23 at the end of drug delivery. As delivery plunger 12 and/or button 23 are substantially fully depressed (i.e., axially translated in the distal direction as per the solid arrow in FIGS. 6D and 7D) to inject fluid from inner chamber 110, one or both may contact flex member 31. Through this contact, flex member 31 is moved radially outwardly (in the direction of the hollow arrow in FIGS. 6D and 7D) and out of engagement with locking window 29 of pill housing 20. This disengagement allows compressed spring 21 to decompress and push against pill housing to thereby push against and retract delivery plunger 12 and/or button 23. Mixing plunger 30 remains substantially in contact or connection with flange connector 25 and/or barrel extension 126, while delivery plunger 12 coupled to needle body 411 and retractable needle 410 comprising cannula 413 is axially retracted in the proximal direction by decompression of spring 21, thereby retracting retractable needle 410. FIGS. 6E and 7E show the substantially final positions of such components after the mixing, drug delivery, and needle retraction stages are complete.

Figure 9A:
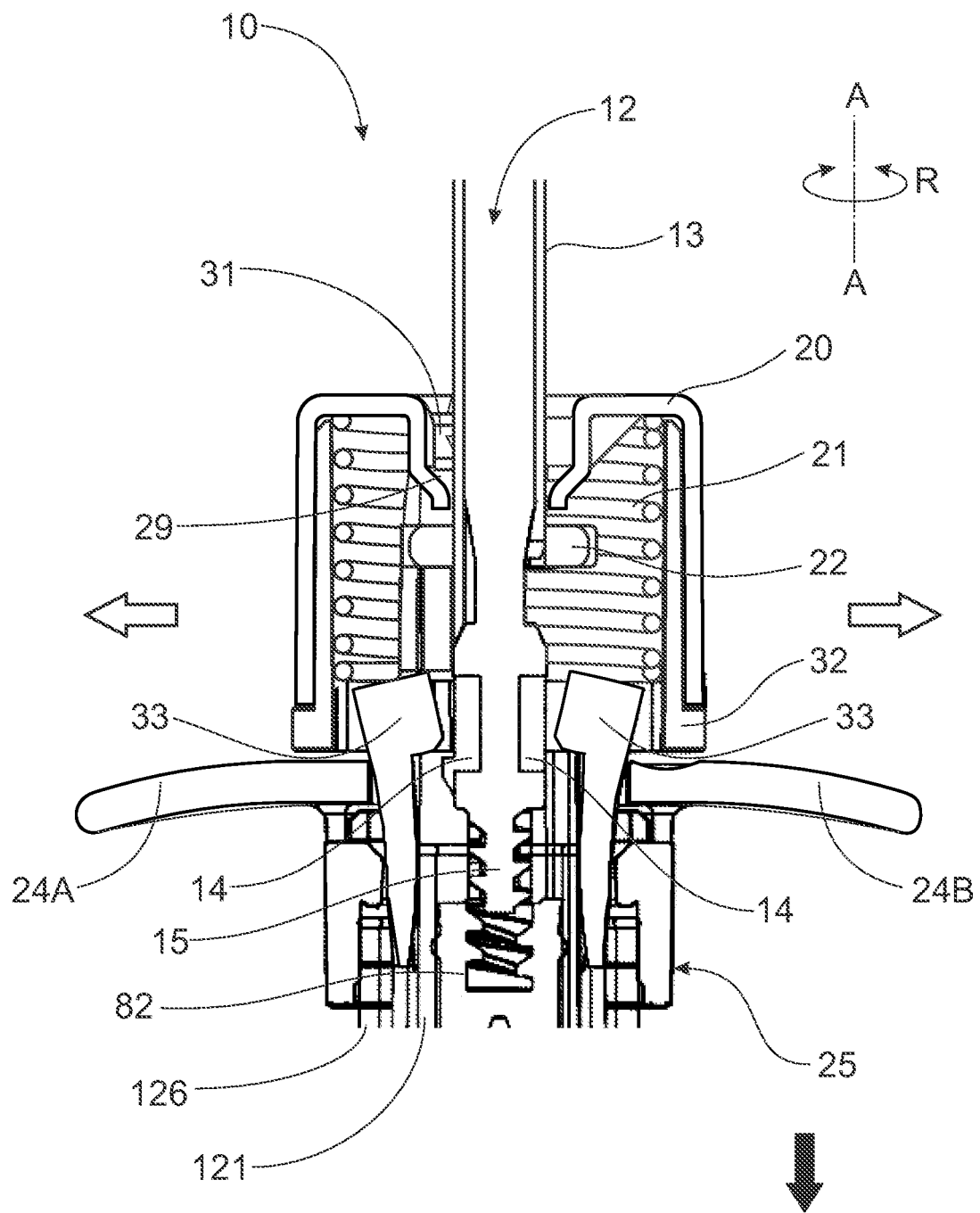
FIG. 9A shows an enlarged sectional view of the disengagement between the mixing plunger and the delivery plunger components of the combination plunger device, according to at least one embodiment of the present invention.
Figure 9B:
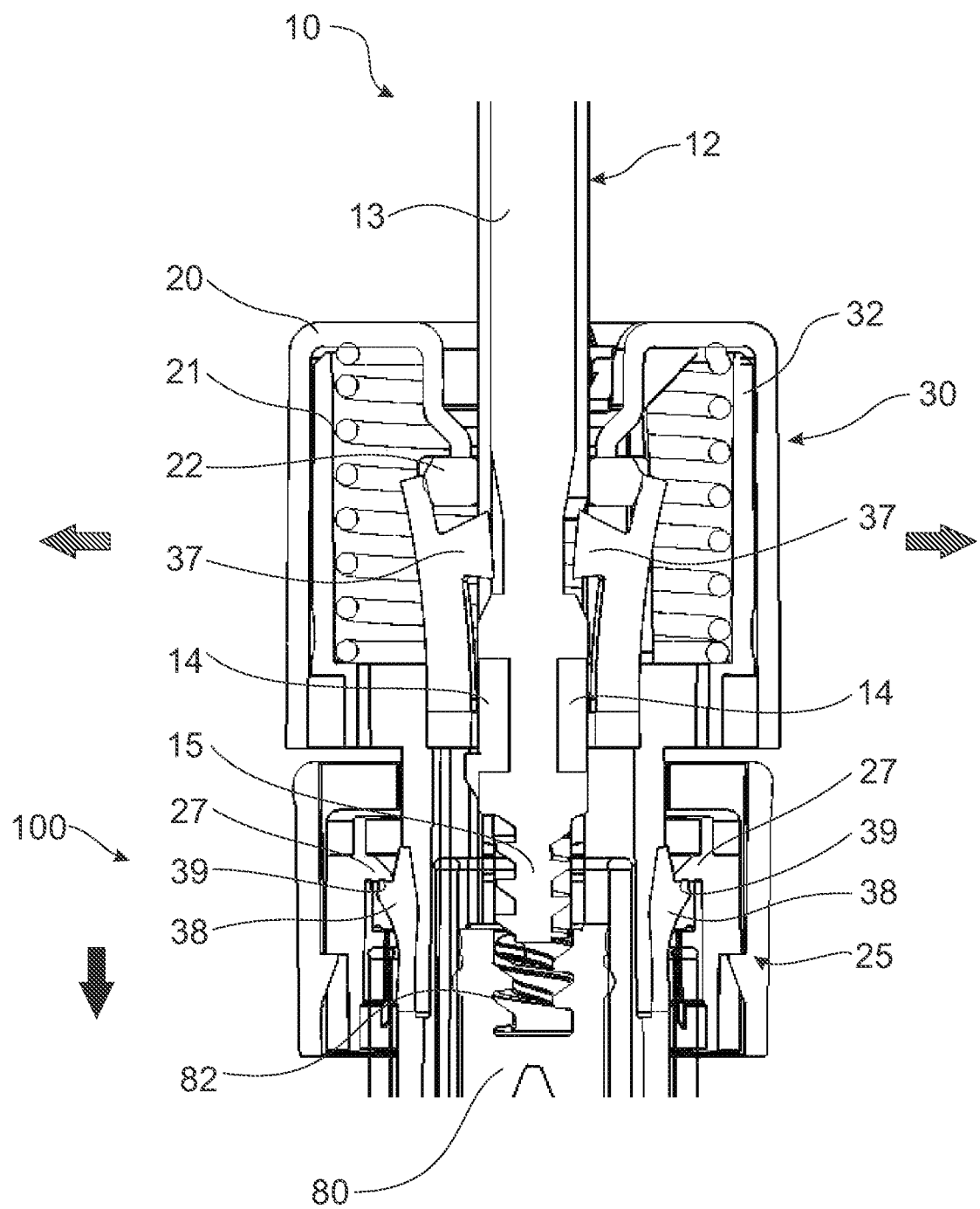
FIG. 9B shows a 90 degree rotated view of the embodiment shown in FIG. 9A.
Figure 10:
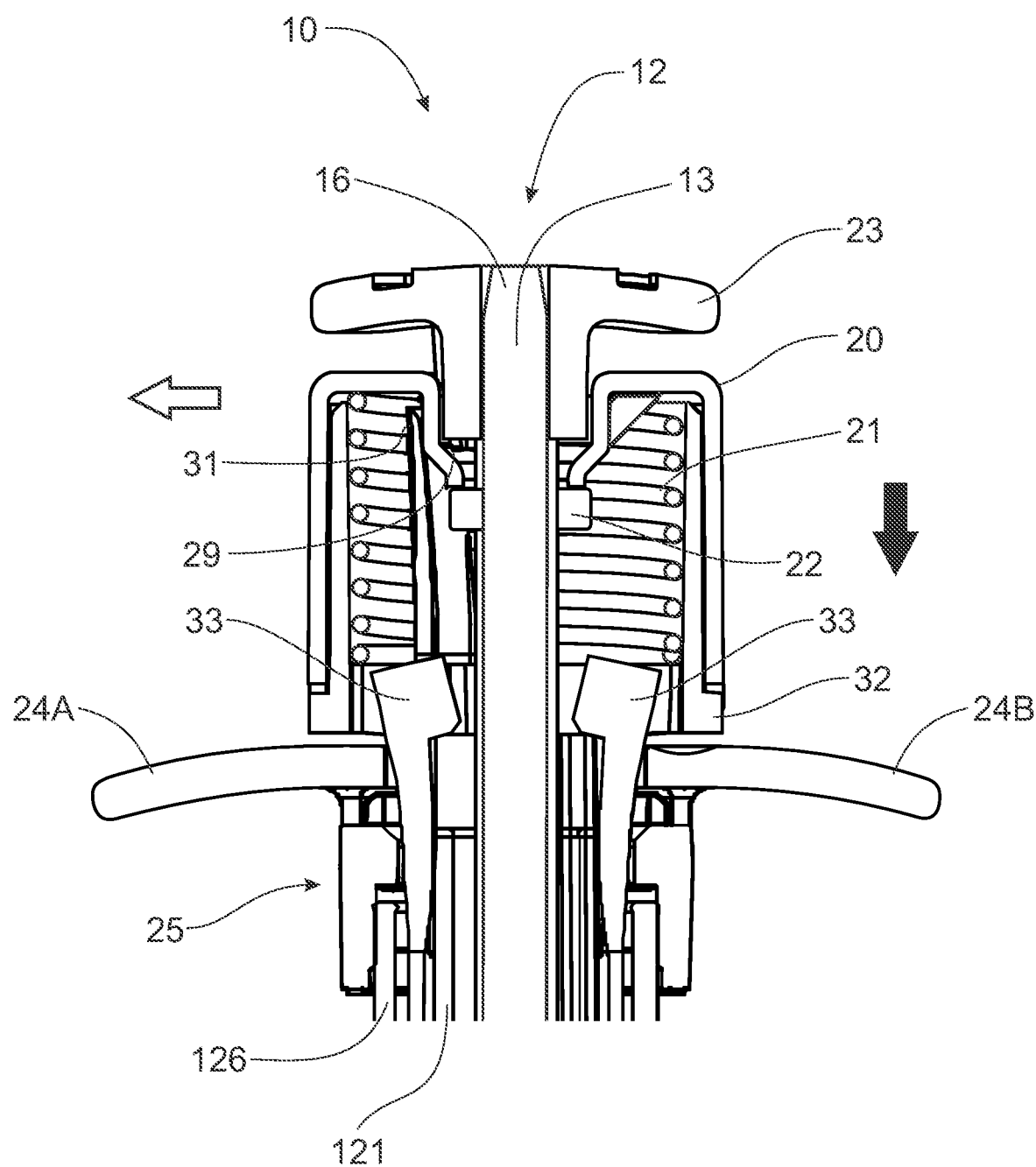
FIG. 10 shows an enlarged sectional view of the disengagement between the flex member of the mixing plunger and the pill housing, which disengagement permits the biasing member to expand in a proximal direction from its initial energized state.
Figure 11A:
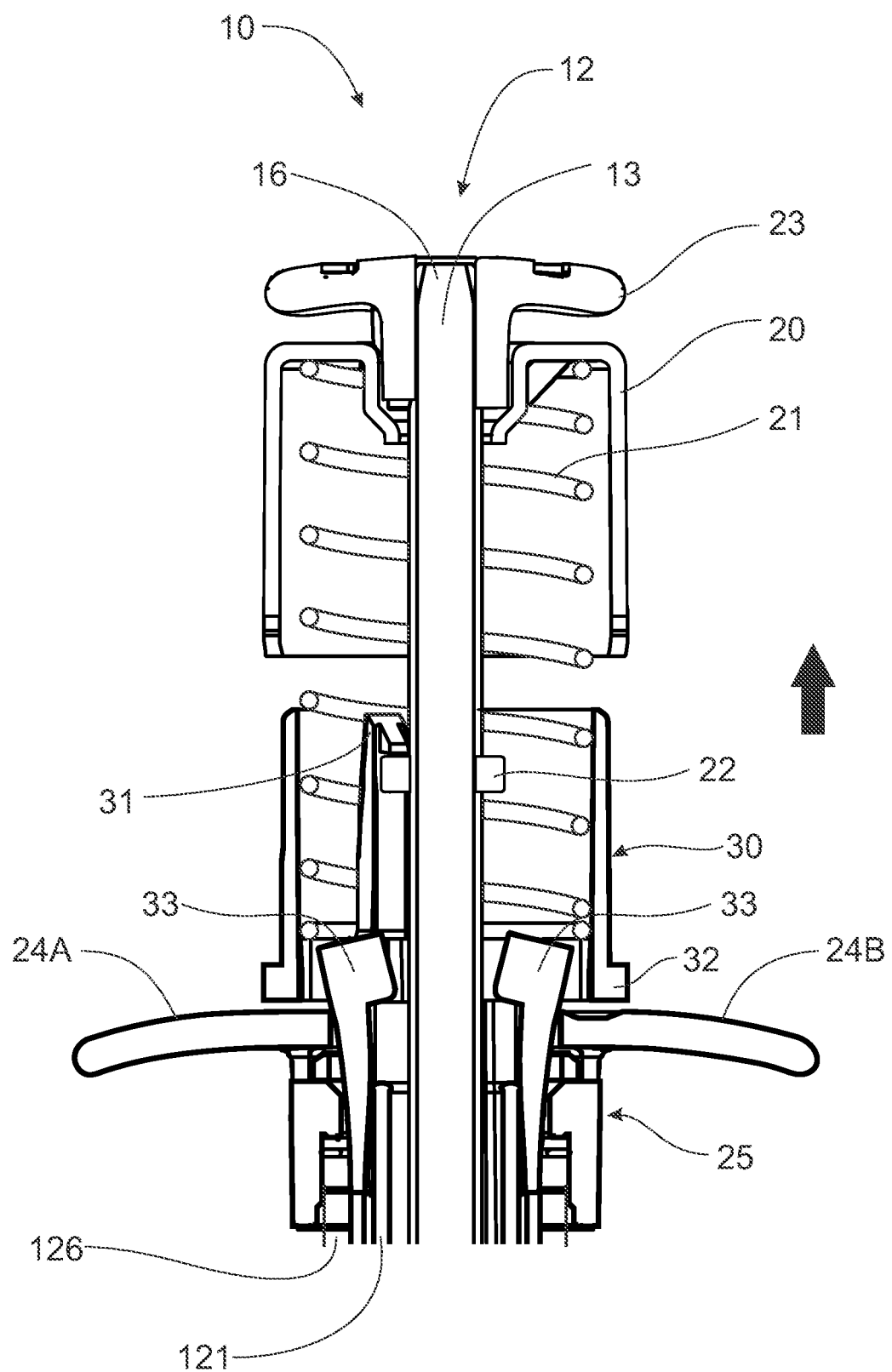
FIG. 11A shows an enlarged sectional view of the final position of a retractable mixing syringe comprising a combination plunger device.

Suitably, retractable mixing syringe 1000 comprises one or more locks or locking systems for mixing plunger 30 and/or delivery plunger 12. As shown in FIG. 9A, connection members 33 initially lock mixing plunger 30 to delivery plunger 12 by releasable connection to connection recesses 14. Connection members 33 are caused to flex radially outwardly (in the direction of hollow arrows), such as by contact with the inner barrel wall 111 near or at the end of the mixing stage. After disengagement, delivery plunger 12 is permitted to be rotated around axis A and/or further depressed in the axial direction. As previously described, biasing member 21 is initially retained in a compressed, energized state between head 32 of mixing plunger 30 and pill housing 20. These components are held in releasable engagement by flex member 31 connecting into pill housing 20 at locking window 29. During operation, the delivery plunger 12 may be rotated, thereby rotating the cam clip 22. Rotation of the cam clip 22 causes lock-out members 37 to be flexed or biased out-wards from the axis by cam clip 22 in the direction shown by the hatched arrows. As shown in FIG. 9B, the rotation of the cam clip 22 thereby disengages the lock-out members 37 from the delivery plunger 12. Disengagement of these components is facilitated by proximal end 16 of delivery plunger 12 and/or button 23 at the end of drug delivery. As delivery plunger 12 and/or button 23 are substantially fully depressed (i.e., axially translated in the distal direction as per the solid arrow in FIGS. 9 and 10) to inject fluid from inner chamber 110, one or both may contact flex member 31. Through this contact, flex member 31 is moved radially outwardly (in the direction of the hollow arrow in FIG. 10) and out of engagement with locking window 29 of pill housing 20 to allow spring 21 to decompress and push against pill housing 20 to thereby push against and retract delivery plunger 12 and/or button 23, as previously described. FIG. 11A shows the substantially final positions of such components after the mixing, drug delivery, and needle retraction stages are complete. The solid arrow indicates the direction of retraction of delivery plunger 12.

Figure 11B:
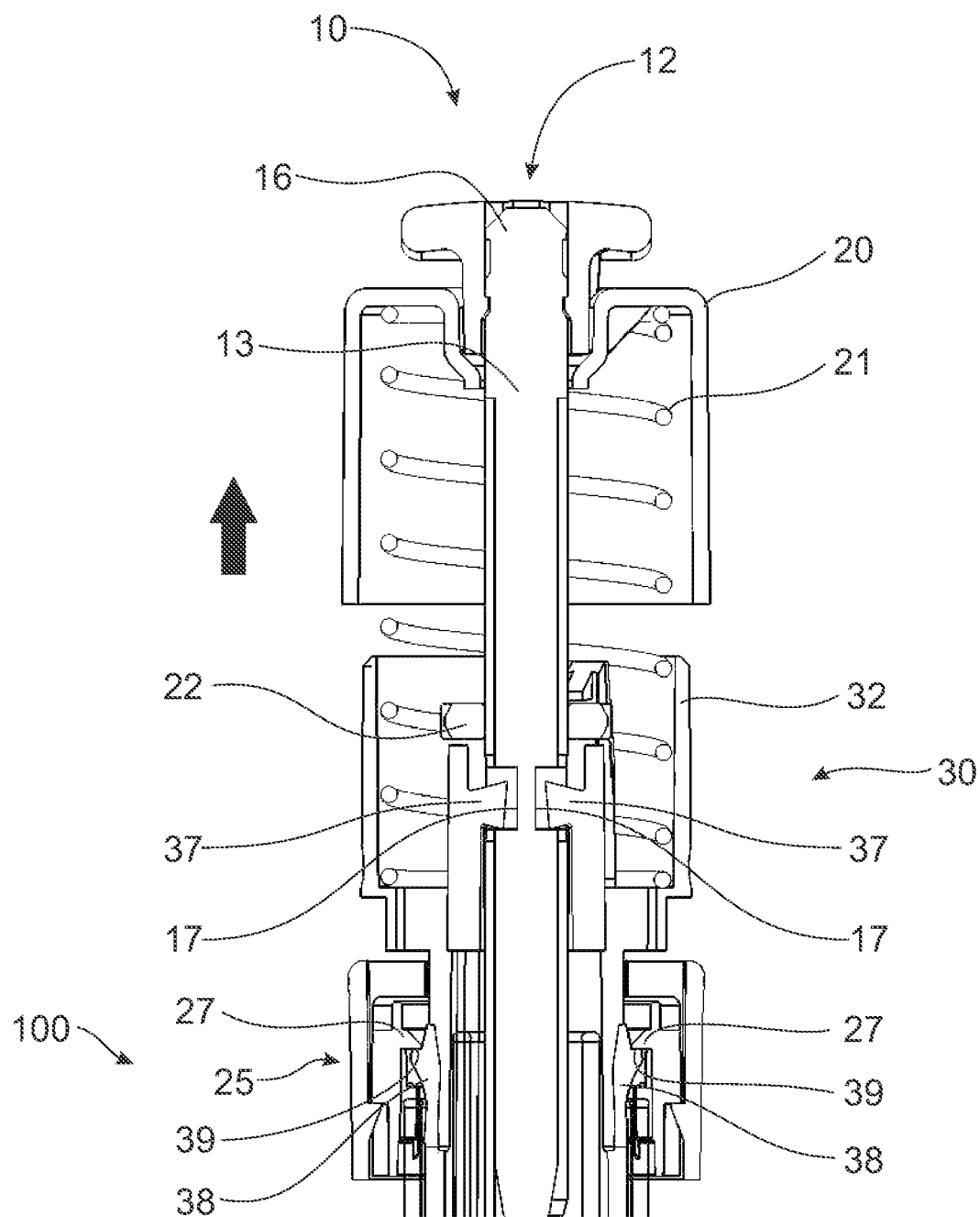
FIG. 11B shows a 90 degree rotated view of the embodiment shown in FIG. 11A.

FIG. 11B shows a 90 degree rotated view of the embodiment shown in FIG. 11A. After release of the pill housing 20, cam clip 22 will be permitted to translate proximally to release lock-out members 37. Lock-out members 37 will be permitted to engage corresponding lock-out recesses 17 of delivery plunger 12, to prevent delivery plunger 12 from moving distally after drug delivery and needle retraction. The cam clip 22 and lock-out members 37 may be configured to provide tactile and/or audible feedback to inform the user that the device has been locked-out. Flex member 31 abuts cam clip 22 to keep cam clip 22 in place and, thereby, further prevent the delivery plunger 12 from being withdrawn or moved proximally from the combination plunger device 10. This provides a useful, optional, safety feature to the combination plunger device 10. Alternatively, or additionally, other safety features may be utilized within the embodiments of the present invention. As previously described, the combination plunger, mixing device and/or mixing syringe may comprise one or more locking systems. For example, the one or more locking systems may comprise elements located on the finger flange 24A, 24B, as part of the flange connector 25, and/or incorporated as a feature of the barrel extension 126. As shown in FIG. 9B and FIG. 11B, one embodiment of the one or more locking systems comprises locking fingers 38 having abutment surfaces 39 that engage respective inner tabs 27 to thereby prevent withdrawal of mixing plunger 30 from mixing device 100.

Certain other variations of mixing syringe 100 are contemplated. As an alternative variation, at the end of depression mixing plunger 30 may be locked to outer barrel 120 by way of complementary detent aspects (not shown) which engage at a point of axial travel in the distal direction by mixing plunger 30 to prevent subsequent axial travel in the proximal direction. These complementary detents may be used together with, or as an alternative to, the locking prongs described previously. In yet another variation, barrel extension 126 may include the aforementioned complementary detent aspects (not shown) of outer barrel 120 which engage mixing plunger 30 upon full axial translation of mixing plunger in the distal direction.

In yet another variation, inner chamber 140 may be compartmentalized (i.e., comprising a plurality of compartments) such as by one more frangible or porous membranes, walls, sealing members or the like, with each compartment containing a different fluid or solid substance, whereby depression of mixing plunger 30 facilitates mixing of each different fluid or solid substance. Additionally, or alternatively, inner chamber 112 may be similarly compartmentalized, each compartment comprising a different fluid or solid substance. Accordingly, mixing device 100 may include two or more substances for mixing and injection.

Assembly and/or manufacturing of combination plunger device 10, mixing device 100 and/or mixing syringe 1000, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization fluids and processes may be employed during the manufacture of the novel components and devices. To add the one or more apertures to the inner barrel, known drilling or boring methodologies such as mechanical or laser drilling may be employed. Furthermore, known sterilization processes may be employed at one or more of the manufacturing or assembly stages to ensure the sterility of the final product.

The combination plunger device may be assembled, packaged, and transported as a separate component from the remainder of the mixing syringe. In at least one embodiment, the mixing device may be assembled, sterilized, and/or filled as a separate component, and sealed with a sealing membrane for storage and/or transportation. The sealing membrane may be any type of sterile membrane such as a fabric seal, particularly a TYVEK fabric seal, or any other type of sealing sterile membrane. The combination plunger device may then be attached to the mixing device to form a mixing syringe. The sealing membrane may be removed by the user or automatically removed during operation of the mixing syringe, pierced during the assembly or operation of the mixing syringe by manual manipulation by the user or by automatic function of the mixing syringe in operation, or otherwise overcome prior to or during use of the mixing syringe.

A number of known filling processes and equipment may be utilized to achieve the filling steps of the syringe manufacturing process disclosed herein. In one embodiment, the second fluid substance may be filled as a liquid substance and lyophilized in situ using certain barrel heat transfer equipment. The needle assembly, delivery plunger, and other components described in these manufacturing and assembly processes may be as described above or may be a number of similar components which achieve the same functionality as these components.

It will be appreciated from the foregoing that the combination plunger device, mixing device and mixing syringe disclosed herein provide an efficient and easily-operated system for mixing multiple substances prior to delivery by the syringe. There is no need to rotate or otherwise orient the inner and outer barrels prior to use to open or align fluid pathways, unlike in many prior art mixing devices such as those previously described. Rotation is utilized herein only to disengage various parts of the combination plunger through the different stages of operation. Additionally, the positioning of the distal seal relative to the vents in the outer barrel and the apertures in the inner barrel keeps the contents of the mixing device sterile while providing adequate venting, which is in contrast to many prior art mixing devices such as previously described.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method of manufacturing a mixing syringe comprising a combination plunger, the method comprising:
    locating a first mixing substance in an outer chamber of the mixing syringe and inserting a first or proximal seal in the outer chamber of the mixing syringe in contact with the first mixing substance;
    locating a second mixing substance in an inner chamber of the mixing syringe and inserting a plunger seal in the inner chamber;
    disposing the combination plunger at a distal end of the mixing syringe, the combination plunger comprising a delivery plunger and a mixing plunger, the delivery plunger initially releasably engaged with the mixing plunger, connection members of the mixing plunger engaging the delivery plunger to prevent rotation of the delivery plunger with respect to the mixing plunger;
    the disposing including aligning the delivery plunger of the combination plunger for axial translation within the inner chamber, wherein the delivery plunger is initially proximal to one or more apertures of the inner chamber and capable of connecting to the plunger seal, and
    mounting the mixing plunger of the combination plunger in the outer chamber, wherein the mixing plunger contacts the first or proximal seal.

2. The method of claim 1, wherein disposing the combination plunger at the distal end of the mixing syringe further comprises connecting a flange connector of the combination plunger to a barrel extension of the mixing syringe.

3. The method of claim 1, further comprising, after locating the second mixing substance in the inner chamber of the mixing syringe, sealing the mixing syringe with a sealing membrane.

4. The method of claim 3, further comprising removing the sealing membrane prior to connecting the delivery plunger to the plunger seal.

5. The method of claim 3, wherein, the sealing membrane is disposed to be pierced by the delivery plunger during operation of the mixing syringe.

6. The method of claim 1, further comprising affixing a vent cap comprising one or more vents to a portion of the inner barrel distal of the one or more apertures.

7. The method of claim 6, wherein the vent cap is connected to a distal end of the outer barrel.

8. The method of claim 1, further comprising inserting a needle assembly into the inner chamber distal of the one or more apertures.

9. A method of manufacturing a mixing syringe comprising a combination plunger, the method comprising:
    locating a first mixing substance in an outer chamber of the mixing syringe and inserting a first or proximal seal in the outer chamber of the mixing syringe in contact with the first mixing substance;
    locating a second mixing substance in an inner chamber of the mixing syringe and inserting a plunger seal in the inner chamber;
    sealing the mixing syringe with a sealing membrane,
    aligning a delivery plunger of the combination plunger for axial translation within the inner chamber, wherein the delivery plunger is initially proximal to one or more apertures of the inner chamber and capable of piercing the sealing membrane during operation and connecting to the plunger seal, and
    mounting a mixing plunger of the combination plunger in the outer chamber, wherein the mixing plunger contacts the first or proximal seal.

10. A method of manufacturing a mixing syringe comprising a combination plunger, the method comprising:
    locating a first mixing substance in an outer chamber of the mixing syringe and inserting a first or proximal seal in the outer chamber of the mixing syringe in contact with the first mixing substance;
    locating a second mixing substance in an inner chamber of the mixing syringe and inserting a plunger seal in the inner chamber;
    aligning a delivery plunger of the combination plunger for axial translation within the inner chamber, wherein the delivery plunger is initially proximal to one or more apertures of the inner chamber and capable of connecting to the plunger seal,
    mounting a mixing plunger of the combination plunger in the outer chamber, wherein the mixing plunger contacts the first or proximal seal, and
    affixing a vent cap comprising one or more vents to a portion of the inner barrel distal of the one or more apertures.

11. The method of claim 10, wherein the vent cap is connected to a distal end of the outer barrel.

* * * * *